United States Patent
Bloxham et al.

(10) Patent No.: US 8,063,247 B2
(45) Date of Patent: Nov. 22, 2011

(54) BICYCLIC ARYL AND HETEROARYL RECEPTOR MODULATORS

(75) Inventors: Jason Bloxham, Oxford (GB); Stuart Edward Bradley, Oxford (GB); Thomas Martin Krulle, Oxford (GB); Martin James Procter, Oxford (GB); Colin Peter Sambrook-Smith, Oxford (GB); Karen Lesley Schofield, Oxford (GB); Donald Smyth, Oxford (GB)

(73) Assignee: Prosidion Limited, Oxford (GB)

( * ) Notice: Subject to any disclaimer, the term of this patent is extended or adjusted under 35 U.S.C. 154(b) by 0 days.

(21) Appl. No.: 12/676,618

(22) PCT Filed: Sep. 8, 2008

(86) PCT No.: PCT/GB2008/050801
§ 371 (c)(1), (2), (4) Date: Jun. 30, 2010

(87) PCT Pub. No.: WO2009/030962
PCT Pub. Date: Mar. 12, 2009

(65) Prior Publication Data
US 2010/0267780 A1   Oct. 21, 2010

(30) Foreign Application Priority Data

Sep. 7, 2007 (GB) .................................. 0717412.1
Sep. 7, 2007 (GB) .................................. 0717413.9

(51) Int. Cl.
C07C 233/65 (2006.01)
C07D 213/02 (2006.01)
A61K 31/44 (2006.01)
A61K 31/165 (2006.01)

(52) U.S. Cl. ......... 564/163; 546/336; 514/357; 514/619

(58) Field of Classification Search .................. 514/357, 514/619; 564/163; 546/336
See application file for complete search history.

(56) References Cited

U.S. PATENT DOCUMENTS

| | | | |
|---|---|---|---|
| 6,028,175 | A | 2/2000 | Grandy et al. |
| 6,225,080 | B1 | 5/2001 | Uhl et al. |
| 2006/0217372 | A1 | 9/2006 | Blanco-Pillado et al. |
| 2010/0113512 | A1 | 5/2010 | Ignar |
| 2010/0173886 | A1 | 7/2010 | Bloxham et al. |

FOREIGN PATENT DOCUMENTS

| | | |
|---|---|---|
| EP | 0843726 B1 | 5/1998 |
| WO | WO-9507983 A1 | 3/1995 |
| WO | WO-9707212 A1 | 2/1997 |
| WO | WO-03101963 A1 | 12/2003 |
| WO | 2004026305 A | 4/2004 |
| WO | WO-2004080968 A1 | 9/2004 |
| WO | WO-2004080996 A1 | 9/2004 |
| WO | WO-2005061442 A1 | 7/2005 |
| WO | WO-2005066164 A1 | 7/2005 |
| WO | WO-2005090286 A1 | 9/2005 |
| WO | WO-2005090303 A1 | 9/2005 |
| WO | WO-2005090337 A1 | 9/2005 |
| WO | WO-2005092836 A1 | 10/2005 |
| WO | WO-2007047397 A2 | 4/2007 |
| WO | 2008021849 A | 2/2008 |
| WO | WO-2008021851 A2 | 2/2008 |
| WO | WO-2008032156 A1 | 3/2008 |
| WO | 2008059335 A | 5/2008 |

OTHER PUBLICATIONS

International Search Report in PCT/GB2008/050801.
International Preliminary Report on Patentability and Written Opinion of the International Searching Authority in PCT/GB2008/050801.
Diaz et al., "SAR and biological evaluation of novel *trans*-3,4-dimethyl-4-arylpiperidine derivatives as opioid antagonists." *Bioorg. Med. Chem. Lett.*, 15:3844-3848 (2005).
Takeuchi et al., "Structure-activity relationship studies of carboxamido-biaryl ethers as opioid receptor antagonists (OpRAs). Part 2", *Bioorg. Med. Chem. Lett.*, 17:6841-6846 (2007).
Takeuchi et al., "Structure-activity relationship studies of carboxamido-biaryl ethers as opioid receptor antagonists (OpRAs). Part I", *Bioorg. Med. Chem. Lett.*, 17:5349-5352 (2007).
Zhang et al., "The μ-opioid receptor subtype is required for the anorectic effect of an opioid receptor antagonist", *Eur. J. Pharmacol.*, 545:147-152 (2006).

*Primary Examiner* — Shailendra Kumar
(74) *Attorney, Agent, or Firm* — Mintz, Levin, Cohn, Ferris, Glovsky and Popeo, P.C.; Ivor R. Elrifi

(57) ABSTRACT

Compounds of formula (I) or pharmaceutically acceptable salts thereof, are opioid receptor modulators, e.g. mu-opioid receptor antagonists, neutral antagonists or inverse agonists, and are useful inter alia for the treatment of obesity.

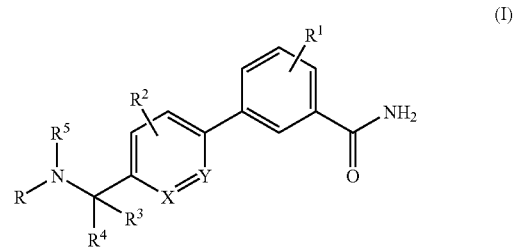

(I)

21 Claims, No Drawings

BICYCLIC ARYL AND HETEROARYL RECEPTOR MODULATORS

This application is a 371 of PCT/GB08/50801, filed Sep. 8, 2008.

BACKGROUND OF THE INVENTION

The present invention is directed to bicyclic aryl and heteroaryl compounds which are opioid receptor modulators, e.g. mu-opioid receptor antagonists, that are useful for the treatment of obesity.

Obesity is characterized by an excessive adipose tissue mass relative to body size. Clinically, body fat mass is estimated by the body mass index (BMI; weight (kg)/height $(m)^2$), or waist circumference. Individuals are considered obese when the BMI is greater than 30 and there are established medical consequences of being overweight. It has been an accepted medical view for some time that an increased body weight, especially as a result of abdominal body fat, is associated with an increased risk for diabetes, hypertension, heart disease, and numerous other health complications, such as arthritis, stroke, gallbladder disease, muscular and respiratory problems, back pain and even certain cancers.

Pharmacological approaches to the treatment of obesity have been mainly concerned with reducing fat mass by altering the balance between energy intake and expenditure. Many studies have clearly established the link between adiposity and the brain circuitry involved in the regulation of energy homeostasis. Direct and indirect evidence suggest that serotonergic, dopaminergic, adrenergic, cholinergic, endocannabinoid, opioid, and histaminergic pathways in addition to many neuropeptide pathways (e.g. neuropeptide Y and melanocortins) are implicated in the central control of energy intake and expenditure. Hypothalamic centres are also able to sense peripheral hormones involved in the maintenance of body weight and degree of adiposity, such as insulin and leptin, and fat tissue derived peptides.

There is a continuing need for novel antiobesity agents, particularly ones that are well tolerated with few adverse effects.

Mu-, kappa- and delta-opioid receptors have been implicated in a number of disease states and their modulation is a potential target for therapeutic intervention.

Antagonists of opioid receptors, in particular the mu-opioid receptor have been shown to reduce body weight in animal models of obesity (J. Zhang et al, *European Journal of Pharmacology*, 454 (2006) 147-152).

Antagonists of opioid receptors have thus been suggested as useful for the treatment of obesity and related disorders, and other diseases or disorders including substance abuse, alcohol abuse, compulsive gambling, depression, opiate overdose, septic shock, irritable bowel syndrome, nausea, vomiting and stroke.

SUMMARY OF THE INVENTION

Compounds of formula (I):

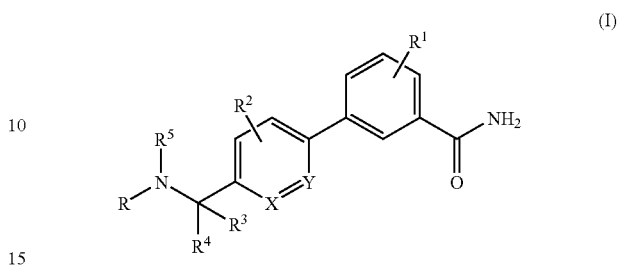

or pharmaceutically acceptable salts thereof, are opioid receptor modulators, e.g. mu-opioid receptor antagonists, neutral antagonists or inverse agonists, and are useful inter alia for the treatment of obesity.

DETAILED DESCRIPTION OF THE INVENTION

The present invention is directed to a compound of formula (I), or a pharmaceutically acceptable salt thereof:

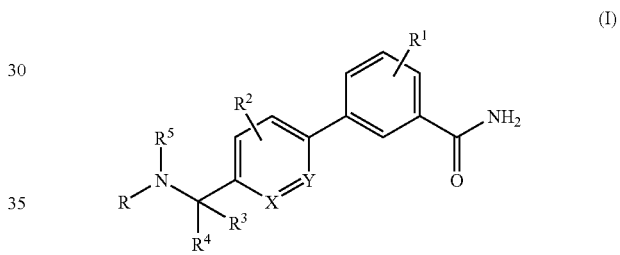

wherein X and Y are CH, or one of X and Y is N and the other is CH;

R is $(CR^7R^8)_nR^6$;

n is 0, 1, 2 or 3;

when n is 0, $R^6$ is $C_3$-$C_{10}$ cycloalkyl;

when n is 1, 2 or 3, $R^6$ is $C_6$-$C_{10}$ aryl, $C_5$-$C_{10}$ heteroaryl, $C_3$-$C_{10}$ cycloalkyl, a 4- to 7-membered oxygen containing heterocycle or $C_1$-$C_6$ alkyl;

wherein any $R^6$ groups are optionally substituted with one to three substituents selected from $C_1$-$C_6$ alkyl, $C_1$-$C_6$ alkoxy, $C_1$-$C_6$ haloalkyl, $C_1$-$C_6$ haloalkoxy and halogen;

$R^1$ is hydrogen, $C_1$-$C_3$ alkyl or halogen;

$R^2$ is hydrogen, $C_1$-$C_3$ alkyl or halogen;

$R^3$ and $R^4$ are independently selected from hydrogen and $C_1$-$C_3$ alkyl;

$R^5$ is hydrogen, $C_1$-$C_6$ alkyl or —$C_2$-$C_3$ alkyl-O—$C_1$-$C_3$ alkyl; and $R^7$ and $R^8$ are independently selected from hydrogen and $C_1$-$C_3$ alkyl, or when n is 2 or 3 one of $R^7$ and $R^8$ may be hydroxy, provided the hydroxy group is not attached to the carbon adjacent to N—$R^5$.

The molecular weight of the compounds of formula (I) is preferably less than 800, more preferably less than 600, even more preferably less than 500.

In the compounds of formula (I):

When $R^1$ is other than hydrogen, it is preferably not ortho to the amide group and para to the ring junction.

When n is 0, $R^6$ is preferably optionally substituted cyclohexyl or indanyl.

When n is 1, 2 or 3, then $R^7$ and $R^8$ are preferably hydrogen or $C_1$-$C_3$ alkyl, more preferably hydrogen.

When n is 1, $R^6$ is preferably optionally substituted $C_6$-$C_{10}$ aryl e.g. phenyl, $C_5$-$C_{10}$ heteroaryl e.g. benzothienyl, thienyl, indazole or indole, or $C_3$-$C_{10}$ cycloalkyl e.g. cyclohexyl.

When n is 2, $R^6$ is preferably optionally substituted $C_6$-$C_{10}$ aryl e.g. phenyl, $C_5$-$C_{10}$ heteroaryl e.g. benzothienyl, thienyl, indazole or indole, $C_3$-$C_{10}$ cycloalkyl e.g. cyclopentyl, cyclohexyl or adamantyl, $C_1$-$C_6$ alkyl or a 4- to 7-membered oxygen containing heterocycle.

When n is 3, $R^6$ is preferably optionally substituted $C_6$-$C_{10}$ aryl e.g. phenyl, or $C_3$-$C_{10}$ cycloalkyl e.g. cyclohexyl.

$R^2$ is preferably hydrogen, methyl or halo, e.g. fluoro.

Subsets of the compounds of formula (I) which may be mentioned are those where X and Y are CH, where X is N and Y is CH, and where X is CH and Y is N.

When X is N then $R^2$ is preferably hydrogen or methyl, when X and Y are CH then $R^2$ is preferably hydrogen, methyl or fluoro, and when Y is N then $R^2$ is preferably hydrogen or methyl.

$R^3$ and $R^4$ are preferably hydrogen.

$R^5$ is preferably hydrogen or methyl.

$R^7$ and $R^8$ are preferably independently selected from hydrogen and $C_1$-$C_3$ alkyl.

Specific subsets of compounds of formula (I) which may be mentioned are those where:

$R^1$ is iodo; or $R^2$ is iodo; or one of $R^3$ and $R^4$ is $C_2$-$C_3$ alkyl or both of $R^3$ and $R^4$ are $C_1$-$C_3$ alkyl; or $R^5$ is —$C_2$-$C_3$ alkyl-O—$C_1$-$C_3$ alkyl; or R is $(CR^7R^8)_nR^6$ where n is 1, 2 or 3, and $R^6$ is $C_3$-$C_{10}$ cycloalkyl; or $R^6$ is bicyclic aryl or bicyclic heteroaryl; or when n is 2 or 3, one of $R^7$ and $R^8$ may be hydroxy, provided the hydroxy group is not attached to the carbon adjacent to N—$R^5$;

or any combination of the above.

While the preferred groups for each variable have generally been listed above separately for each variable, preferred compounds of this invention include those in which several or each variable in formula (I) is selected from the preferred groups for each variable. Therefore, this invention is intended to include all combinations of preferred listed groups.

Specific compounds of the invention which may be mentioned are those included in the Examples and pharmaceutically acceptable salts thereof.

As used herein, unless stated otherwise, "alkyl" as well as other groups having the prefix "alk" such as, for example, alkoxy, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

The term "haloalkyl" includes alkyl groups substituted by one or more halo, e.g. fluoro atoms, such as $CH_2F$, $CHF_2$ and $CF_3$. The term "haloalkoxy" should be interpreted accordingly.

The term "halo" includes fluorine, chlorine, bromine and iodine atoms.

The term "cycloalkyl" means carbocycles containing no heteroatoms, and includes monocyclic mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl rings include cyclopropyl, cyclobutyl, cyclopentyl, cyclohexyl, and decahydronaphthyl, adamantyl, indanyl, 1,2,3,4-tetrahydronaphthyl and the like.

The term "aryl" includes phenyl and naphthyl, in particular phenyl.

The term "4- to 7-membered oxygen containing heterocycle" includes 4- to 7-membered saturated rings containing one oxygen atom. Examples of heterocyclic rings include oxetane, tetrahydrofuran, tetrahydropyran and oxepane.

The term "heteroaryl" includes mono- and bicyclic 5- to 10-membered, e.g. monocyclic 5- or 6-membered, heteroaryl rings containing up to 4 heteroatoms selected from N, O and S. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl and triazinyl. Bicyclic heteroaryl groups include bicyclic heteroaromatic groups where a 5- or 6-membered heteroaryl ring is fused to a phenyl or another heteroaromatic group. Examples of such bicyclic heteroaromatic rings are benzofuran, benzothiophene, indole, benzoxazole, benzothiazole, indazole, benzimidazole, benzotriazole, quinoline, isoquinoline, quinazoline, quinoxaline and purine.

Compounds described herein may contain one or more asymmetric centers and may thus give rise to enantiomers, diastereomers and optical isomers. The present invention includes all such possible enantiomers, diastereomers as well as their racemic mixtures, their substantially pure resolved enantiomers, all possible geometric isomers, and pharmaceutically acceptable salts thereof. The above formula (I) is shown without a definitive stereochemistry at certain positions. The present invention includes all stereoisomers of formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of formula (I) exists, the present invention includes any possible tautomers and pharmaceutically acceptable salts thereof, and mixtures thereof, except where specifically drawn or stated otherwise.

When the compound of formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, oxalic, pamoic, pantothenic, phosphoric, succinic, sulfuric, tartaric, p-toluenesulfonic acid and the like.

Since the compounds of formula (I) are intended for pharmaceutical use they are preferably provided in substantially pure form, for example at least 60% pure, more suitably at least 75% pure, especially at least 95% or 98% pure (% are on a weight for weight basis).

The compounds of formula (I) can be prepared as described below.

Compounds of formula (I) can be prepared using the method illustrated in Scheme 1:

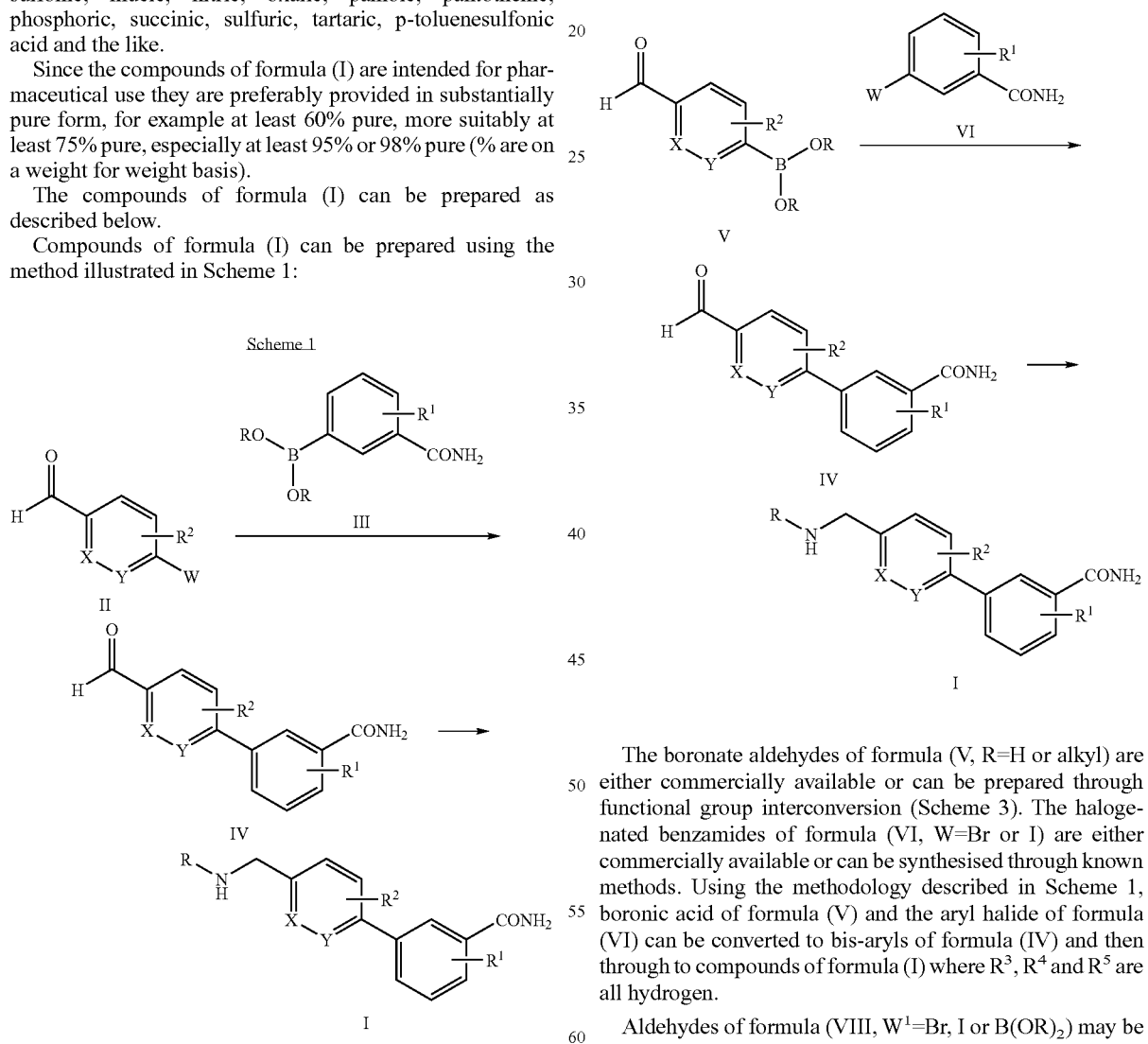

The halogenated aldehydes of formula (II, W=Br or I) are either commercially available or can be readily synthesised through functional group interconversions (Scheme 3). The boronic acid or esters (III) are either commercially available or can be obtained through conversion of the halogen to the boronate using known chemistry (Scheme 4). Treating the boronic acid or ester of formula (III) with an aryl halide of formula (II) in solvents such as dimethoxyethane and ethanol in the presence of a palladium catalyst such as bis(triphenylphosphino)palladium dichloride and a base such as aqueous sodium carbonate at elevated temperatures leads to bi-aryl aldehydes of formula (IV). Reductive amination of the aldehyde of formula (IV) with an amine in a solvent such as methanol and a reducing agent such as sodium borohydride gives compounds of formula (I) where $R^3$, $R^4$ and $R^5$ are all hydrogen. Alternative groups may be used in place of the amide that may later be converted to the amide functionality through known methods, for example, nitrile.

In addition, compounds of formula (I) can be prepared using the method illustrated in Scheme 2:

The boronate aldehydes of formula (V, R=H or alkyl) are either commercially available or can be prepared through functional group interconversion (Scheme 3). The halogenated benzamides of formula (VI, W=Br or I) are either commercially available or can be synthesised through known methods. Using the methodology described in Scheme 1, boronic acid of formula (V) and the aryl halide of formula (VI) can be converted to bis-aryls of formula (IV) and then through to compounds of formula (I) where $R^3$, $R^4$ and $R^5$ are all hydrogen.

Aldehydes of formula (VIII, $W^1$=Br, I or $B(OR)_2$) may be prepared through for example treatment of a halogenated precursor of formula (VII, $X^1$=Br or I) with butyl lithium at low temperature in a solvent such as THF and quenching with DMF. Alternatively nitriles of formula (VII, $X^1$=CN, $W^1$=Br, I or $B(OR)_2$) can be treated with di-isobutylaluminium hydride in a solvent such as toluene to give aldehydes of formula (VIII).

Scheme 3

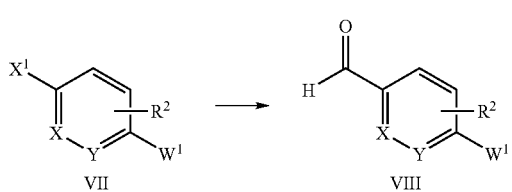

Boronates of formula (X, R¹=alkyl or XII, R¹=alkyl, Z=CN or CONH₂) can be prepared from, for example, either the aryl triflate of formula (IX, W²=OSO₂CF₃ or X¹, W²=OSO₂CF₃, Z=CN or CONH₂) or aryl halide of formula (IX, W²=Br or I or X¹, W²=Br or I, Z=CN or CONH₂) treating with a reagent such as bis(pinacolato)diboron and a palladium catalysts such as palladium acetate and bis(diphenylphosphino)ferrocene palladium dichloride in a solvent such as DMF. Boronic acids of formula (X or XII, R=H) can be prepared from the boronate using known methods.

Scheme 4

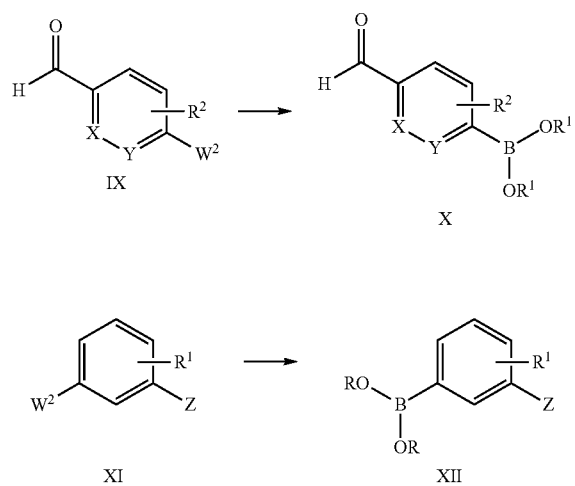

Alternatively the aldehyde of formula (IV) can be treated with ammonia or an ammonia equivalent and a reducing agent such as sodium borohydride in a solvent such as methanol to give the benzylamine of formula (XIII), which can then be converted to compounds of formula (I) through treatment with an aldehyde in a solvent such as methanol with a reducing agent such as sodium borohydride.

Scheme 5

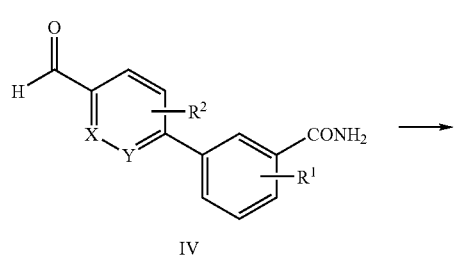

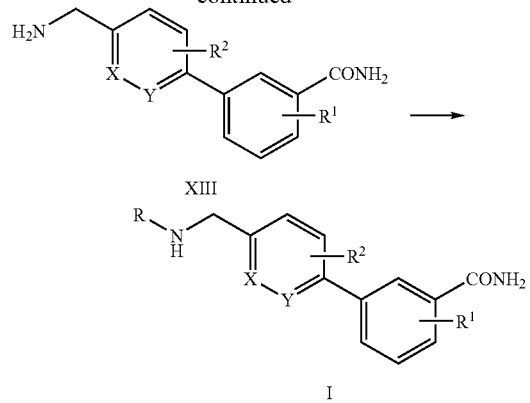

Compounds of the formula (XVI) can be prepared by the procedure outlined in Scheme 6.

Scheme 6

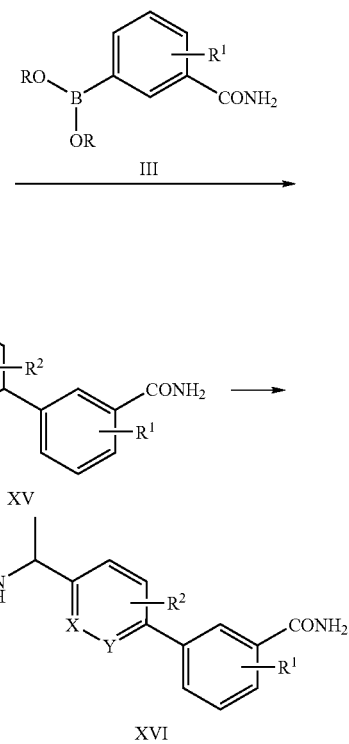

The ketones of formula (XIV, W=Br or I) are either commercially available or can be readily synthesised by known methods. Treating the ketone of formula (XIV) with a boronic acid of formula (III) in solvents such as dimethoxyethane and ethanol in the presence of a palladium catalyst such as bis(triphenylphosphino)palladium dichloride and a base such as aqueous sodium carbonate at elevated temperatures leads to bi-aryl ketones of formula (XV). Reductive amination of the ketone of formula (XV) with an amine and a reducing agent such as sodium borohydride in a solvent such as methanol gives compounds of formula (XVI).

Compounds of formula (XX) can be prepared by the procedure outlined in Scheme 7.

Scheme 7

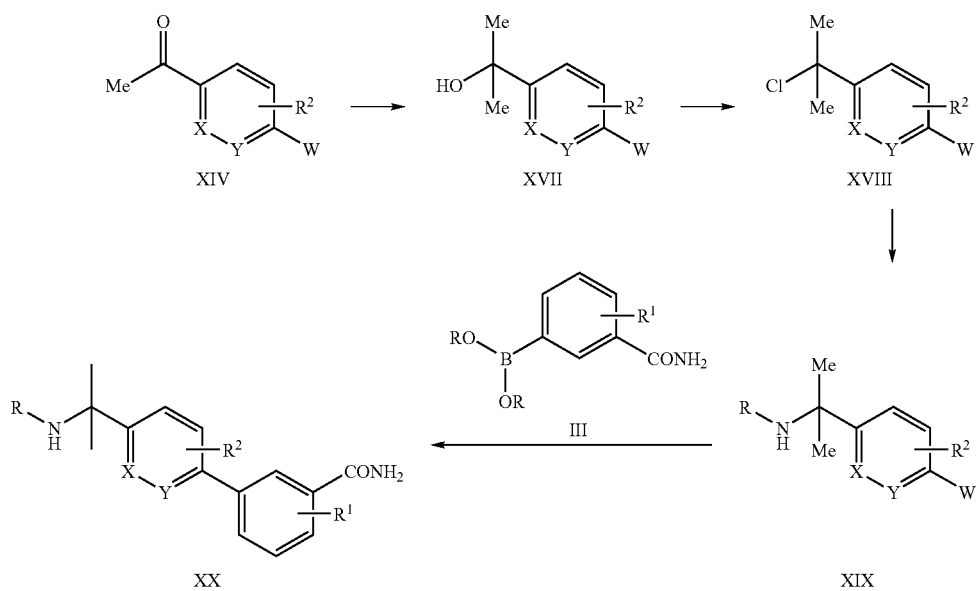

Where both R³ groups are methyl in compounds of formula (I), ketones of formula (XIV, W=Br or I) can be treated with organometallic reagents such as methylmagnesium bromide in a solvent such as THF to give alcohols of formula (XVII). Alcohols of formula (XVII) can be chlorinated by reagents such as thionyl chloride in a solvent such as DCM to give chlorides of formula (XVIII) which can then be treated with the desired amines in a solvent such as DCM and a base such as triethylamine to give benzylamines of formula (XIX). Benzylamines (XIX) can then be treated with the boronic acid in solvents such as dimethoxyethane and ethanol in the presence of a palladium catalyst such as bis(triphenylphosphino)palladium dichloride and a base such as aqueous sodium carbonate at elevated temperatures to give compounds of formula (XX).

Further details for the preparation of the compounds of formula (I) are found in the examples.

The compounds of formula (I) may be prepared singly or as compound libraries comprising at least 2, for example 5 to 1,000, compounds and more preferably 10 to 100 compounds of formula (I). Compound libraries may be prepared by a combinatorial "split and mix" approach or by multiple parallel synthesis using either solution or solid phase chemistry, using procedures known to those skilled in the art.

During the synthesis of the compounds of formula (I), labile functional groups in the intermediate compounds, e.g. hydroxy, carboxy and amino groups, may be protected. The protecting groups may be removed at any stage in the synthesis of the compounds of formula (I) or may be present on the final compound of formula (I). A comprehensive discussion of the ways in which various labile functional groups may be protected and methods for cleaving the resulting protected derivatives is given in, for example, Protective Groups in Organic Chemistry, T. W. Greene and P. G. M. Wuts, (1991) Wiley-Interscience, New York, 2$^{nd}$ edition.

Any novel intermediates as defined above, such as the compounds of formula (II) are also included within the scope of the invention.

The preferences recited above for the compounds of formulae (I) also apply to any intermediate compounds.

As indicated above the compounds of formula (I) are useful as opioid receptor modulators e.g. for the treatment of obesity. For such use the compounds of formula (I) will generally be administered in the form of a pharmaceutical composition.

The invention also encompasses a pharmaceutical composition comprising a compound of formula (I), or a pharmaceutically acceptable salt thereof, in combination with a pharmaceutically acceptable carrier.

Preferably the composition is comprised of a pharmaceutically acceptable carrier and a non-toxic therapeutically effective amount of a compound of formula (I), or a pharmaceutically acceptable salt thereof.

Moreover, the invention also provides a pharmaceutical composition for the treatment of disease by modulating opioid receptors, e.g. resulting in the treatment of obesity, comprising a pharmaceutically acceptable carrier and a non-toxic therapeutically effective amount of compound of formula (I), or a pharmaceutically acceptable salt thereof.

The pharmaceutical compositions may optionally comprise other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds of formula (I), or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous).

Thus, the pharmaceutical compositions can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound of formula (I), or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The compounds of formula (I), or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, using a compound of formula (I), or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient.

Compositions containing a compound of formula (I), or pharmaceutically acceptable salts thereof, may also be prepared in powder or liquid concentrate form.

Generally, dosage levels on the order of 0.01 mg/kg to about 150 mg/kg of body weight per day are useful in the treatment of the above-indicated conditions, or alternatively about 0.5 mg to about 7 g per patient per day. For example, obesity may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of formula (I), may be used in the treatment of diseases or conditions in which opioid receptors play a role.

Thus the invention also provides a method for the treatment of a disease or condition in which opioid receptors play a role comprising a step of administering to a subject in need thereof an effective amount of a compound of formula (I), or a pharmaceutically acceptable salt thereof.

Diseases or conditions in which opioid receptors play a role include obesity. In the context of the present application the treatment of obesity is intended to encompass the treatment of diseases or conditions such as obesity and other eating disorders associated with excessive food intake e.g. by reduction of appetite and body weight, maintenance of weight reduction and prevention of rebound.

The compounds of the invention may also be used for treating of other diseases related to obesity including metabolic diseases such as Type II diabetes, metabolic syndrome (syndrome X), impaired glucose tolerance, dyslipidemia, hyperlipidemia, hypertriglyceridemia, hypercholesterolemia, low HDL levels and hypertension.

Other diseases or conditions in which opioid receptors play a role include substance abuse, alcohol abuse, compulsive gambling, depression, opiate overdose, septic shock, irritable bowel syndrome, nausea, vomiting and stroke.

The invention also provides a method for the regulation of feeding and/or satiety comprising a step of administering to a subject in need thereof an effective amount of a compound of formula (I), or a pharmaceutically acceptable salt thereof.

The invention also provides a method for the treatment of obesity comprising a step of administering to a subject in need thereof an effective amount of a compound of formula (I), or a pharmaceutically acceptable salt thereof.

The invention also provides a method for the treatment of a metabolic disease selected from Type II diabetes, metabolic syndrome (syndrome X), impaired glucose tolerance, dyslipidemia, hyperlipidemia, hypertriglyceridemia, hypercholesterolemia, low HDL levels and hypertension, comprising a step of administering to a subject in need thereof an effective amount of a compound of formula (I), or a pharmaceutically acceptable salt thereof.

The invention also provides the use of a compound of formula (I), or a pharmaceutically acceptable salt thereof, in the treatment of a condition as defined above.

The invention also provides the use of a compound of formula (I), or a pharmaceutically acceptable salt thereof, in the manufacture of a medicament for the treatment of a condition as defined above.

In the methods of the invention the term "treatment" includes both therapeutic and prophylactic treatment.

The compounds of formula (I), or pharmaceutically acceptable salts thereof, may be administered alone or in combination with one or more other therapeutically active compounds. The other therapeutically active compounds may be for the treatment of the same disease or condition as the compounds of formula (I), or a different disease or condition. The therapeutically active compounds may be administered simultaneously, sequentially or separately.

The compounds of formula (I), may be administered with other active compounds for the treatment of obesity and/or diabetes, for example insulin and insulin analogs, gastric lipase inhibitors, pancreatic lipase inhibitors, sulfonyl ureas and analogs, biguanides, α2 agonists, glitazones, PPAR-γ agonists, RXR agonists, fatty acid oxidation inhibitors, α-glucosidase inhibitors, β-agonists, phosphodiesterase inhibitors, lipid lowering agents, glycogen phosphorylase inhibitors, MCH-1 antagonists, CB-1 antagonists, GPR119 agonists, serotonin and noradrenalin reuptake inhibitors, amylin antagonists, lipoxygenase inhibitors, somostatin analogs, glucokinase activators, glucagon antagonists, insulin signalling agonists, PTP1B inhibitors, gluconeogenesis inhibitors, antilypolitic agents, GSK inhibitors, galanin receptor agonists, anorectic agents, CCK receptor agonists, leptin, serotonergic/dopaminergic antiobesity drugs, CRF antagonists, CRF binding proteins, thyromimetic compounds, aldose reductase inhibitors, glucocorticoid receptor antagonists, GLP-1 agonists, DPIV inhibitors, NHE-1 inhibitors or sorbitol dehydrogenase inhibitors.

All publications, including, but not limited to, patents and patent application cited in this specification, are herein incorporated by reference as if each individual publication were specifically and individually indicated to be incorporated by reference herein as fully set forth.

The invention will now be described by reference to the following examples which are for illustrative purposes and are not to be construed as a limitation of the scope of the present invention.

EXAMPLES

Materials and methods

Column chromatography was carried out on $SiO_2$ (40-63 mesh). LCMS data were obtained using a Waters Symmetry 3.5μ $C_{18}$ column (2.1×30.0 mm, flow rate=0.8 mL/min) eluting with a (5% MeCN in $H_2O$)—MeCN solution containing 0.1% $HCO_2H$ over 6 min and UV detection at 220 nm. Gradient information: 0.0-1.2 min: 100% (5% MeCN in $H_2O$); 1.2-3.8 min: Ramp up to 10% (5% MeCN in $H_2O$)—90% MeCN; 3.8-4.4 min: Hold at 10% (5% MeCN in $H_2O$)—90% MeCN; 4.4-5.5 min: Ramp up to 100% MeCN; 5.5-6.0 min: Return to 100% (5% MeCN in $H_2O$). The mass spectra were obtained employing an electrospray ionisation source in either the positive ($ES^+$) or negative ($ES^-$) ion mode. Where chlorine is present in the molecule the masses are quoted for $^{35}Cl$ and when bromine is present $^{79}Br$ has been quoted. Additional LCMS data (LCMS method 2) were obtained using Waters Xterra MS C18, 5 μm (4.6×50 mm, flow rate 1.5 mL/min) eluting with a $H_2O$-MeCN gradient containing 0.1% v/v ammonia over 12 min with UV detection at 215 and 254 nm. Gradient information: 0.0-8.0 min: Ramp from 95% $H_2O$—5% MeCN to 5% $H_2O$—95% MeCN; 8.0-9.9 min: Hold at 5% $H_2O$—95% MeCN; 9.9-10.0 min: Return to 95% $H_2O$—5% MeCN; 10.0-12.0 min: Hold at 95% $H_2O$—5% MeCN. Mass spectra were obtained using an electrospray ionization source in either the positive ($ESI^+$) or negative ($ESI^-$) mode. Prep HPLC purification was carried out using a Lunar 10μ ODS2 (250×21.2 mm; Flow rate=20 mL/min) eluting with solvent A (10% MeCN, 90% water) and solvent B (90% MeCN, 10% water) and UV detection at 215 nm. Gradient information: 0.0-0.2 min: 90% A, 10% B; 0.2-10.0 min: Ramp up to 10% A, 90% B; 10.0-15.0 min: 10% A, 90% B; 15.0-16.0 min: Return to 90% A, 10% B.

Abbreviations and acronyms: AcOH: Acetic acid; MeCN: Acetonitrile; $NH_3$: Ammonia; DCM: Dichloromethane; DAST: Diethyl aminosulphur trifluoride; DIBAL: Diisobutylaluminium hydride; DIPEA: N,N-Diisopropylethylamine; DME: Dimethoxyethane; DMSO: Dimethylsulfoxide; DMF: N,N-Dimethylformamide; Ether: Diethyl ether; EtOH: Ethanol; EtOAc: Ethyl acetate; HCl: Hydrogen chloride; $MgSO_4$: Magnesium sulphate; MeOH: Methanol; $K_2CO_3$: Potassium Carbonate; rt: room temperature; RT: Retention time; $Na_2CO_3$: Sodium carbonate; $NaHCO_3$: Sodium hydrogen carbonate; NaOH: Sodium hydroxide; THF: Tetrahydrofuran; TMEDA: Tetramethylethylene diamine; TFA: Trifluoroacetic acid; Et₃N: Triethylamine.

Preparation 1: 4'-Formylbiphenyl-3-carboxylic acid amide

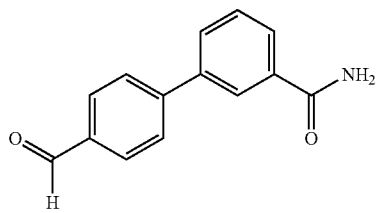

To a solution of 4-bromobenzaldehyde (1.02 g, 5.6 mmol) in toluene (13 mL) and ethanol (13 mL) under argon, was added (3-aminocarbonylbenzene)boronic acid (1.0 g, 6.1 mmol) followed by palladium tetrakis triphenylphosphine (0.64 g, 0.6 mmol) and 2M Na₂CO₃ (13 mL). The mixture was heated to 90° C. for 3 h and then allowed to cool to rt. EtOAc (175 mL) and THF (175 mL) were added and the organics were washed with water (3×40 mL), brine (30 mL) and dried (MgSO₄). The solvent was removed in vacuo. Purification by column chromatography (0.4% NH₃: 4% MeOH: DCM) gave the title compound: RT=3.07 min; m/z (ES⁺)= 226.0 [M+H]⁺.

Preparation 2: Benzyl(4-isopropylcyclohexyl)amine

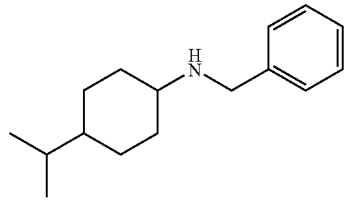

Using the procedure outlined in Example 1, 4-isopropylcyclohexanone and benzylamine were converted to the title compound: RT=2.52 min; m/z (ES⁺)=232.1 [M+H]⁺.

Preparation 3: 4-Isopropylcyclohexylamine hydrochloride salt

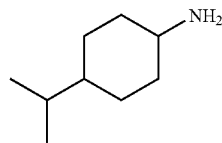

To a solution of benzyl(4-isopropylcyclohexyl)amine (2.39 g, 10.7 mmol) in THF (10 mL) under argon was added 10% palladium-on-carbon (1.14 g, 1.1 mmol). The reaction was then stirred under a hydrogen atmosphere for 16 h. The mixture was filtered through celite and washed with THF (50 mL) and the solvent was removed in vacuo. The residue was dissolved in EtOAc (10 mL) and 1M HCl in ether (5.3 mL) added. The precipitate was filtered off to give the title compound: RT=2.25 min; m/z (ES⁺)=142.1 [M+H]⁺.

Preparation 4: Benzyl(4,4-dimethylcyclohex-2-enyl)amine

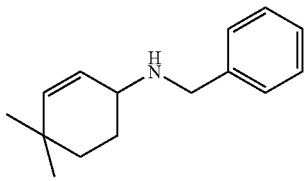

Using the procedure outlined in Example 1, 4,4-dimethyl-2-cyclohexen-1-one and benzylamine were converted to the title compound: RT=2.39 min; m/z (ES⁺)=216.1 [M+H]⁺.

Preparation 5: 4,4-Dimethylcyclohexylamine hydrochloride

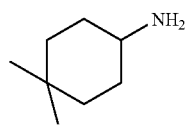

Using the procedure outlined in Preparation 3, benzyl(4,4-dimethylcyclohex-2-enyl)amine was converted to the title compound: RT=1.75 min; m/z (ES⁺)=128.1 [M+H]⁺.

Preparation 6: 3'-Chloro-4'-formylbiphenyl-3-carboxylic acid amide

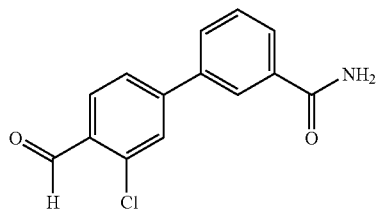

To 4-bromo-2-chlorobenzonitrile (2.0 g, 9.2 mmol) in toluene (50 mL) at −78° C. under argon was added DIBAL (1M solution in toluene, 13.9 mL, 13.9 mmol). The mixture was allowed to warm to −50° C. over 4 h. MeOH (4.5 mL) and water (4.5 mL) were added and the mixture stirred for 10 min at −50° C. The mixture was allowed to warm to rt, acidified with 2N HCl (pH<7) and extracted with EtOAc (200 mL) and water (100 mL). The aqueous was further extracted with EtOAc (2×50 mL), the combined organics were then washed with brine and dried (MgSO₄). The solvent was removed in vacuo and the residue purified by column chromatography (25% DCM: Iso-hexane) to give 4-bromo-2-chlorobenzaldehyde. To a solution of 4-bromo-2-chlorobenzaldehyde (750 mg, 3.4 mmol) in DME (22 mL) and EtOH (15 mL) was added 3-carboxamidobenzene boronic acid (676 mg, 4.1 mmol) and 2M Na₂CO₃ solution (15 mL). Argon was bubbled through the mixture for 15 min. Bis(triphenylphosphino) palladium dichloride (120 mg, 0.17 mmol) was added and the reaction heated to 75° C. for 6.5 h before cooling to rt. The mixture was partitioned between water (200 mL) and EtOAc (200 mL), the aqueous was extracted with EtOAc (2×50 mL) and the combined organics dried (MgSO$_4$). The solvent was removed in vacuo and the residue purified by column chromatography (50% EtOAc: Iso-hexane to 100% EtOAc) to give the title compound: RT=3.19 min; m/z (ES$^+$)=301.0 [M+H+MeCN]$^+$.

Preparation 7: 3'-Fluoro-4'-formylbiphenyl-3-carboxylic acid amide

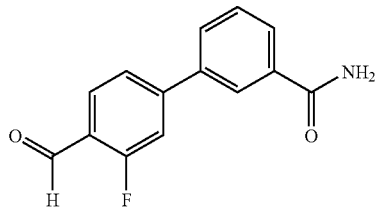

Using the method outlined in Preparation 6, 4-bromo-2-fluorobenzaldehyde and 3-carboxamidobenzene boronic acid were converted to the title compound which was used without further characterisation.

Preparation 8: 3-(6-Formylpyridin-3-yl)benzamide

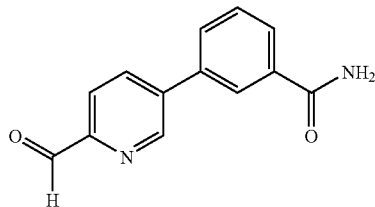

Using the method outlined in Preparation 1, 5-bromopyridine-2-carboxaldehyde and 3-carboxamidobenzene boronic acid were converted to the title compound: RT=2.53 min; m/z (ES$^+$)=227.0 [M+H]$^+$.

Preparation 9: 2'-Fluoro-4'-formylbiphenyl-3-carboxylic acid amide

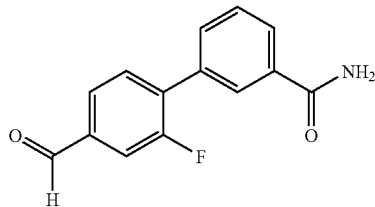

Using the method outlined in Preparation 1, 4-bromo-3-fluorobenzaldehyde and 3-carboxamidobenzene boronic acid were converted to the title compound which was used without further characterisation.

Preparation 10: 4'-Formyl-2'-methylbiphenyl-3-carboxylic acid amide

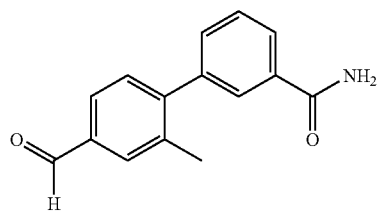

Using the method outlined in Preparation 6, 4-bromo-3-methylbenzonitrile and 3-carboxamidobenzene boronic acid were converted to the title compound: RT=3.01 min; m/z (ES$^+$)=281.0 [M+H+MeCN]$^+$.

Preparation 11: 4'-Formyl-3'-methylbiphenyl-3-carboxylic acid amide

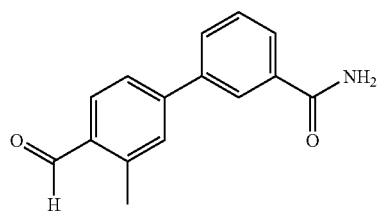

Using the method outlined in Preparation 6, 4-bromo-2-methylbenzonitrile and 3-carboxamidobenzene boronic acid were converted to the title compound: RT=3.11 min; m/z (ES$^+$)=240.0 [M+H]$^+$.

Preparation 12: 3-(5-Formylpyridin-2-yl)benzamide

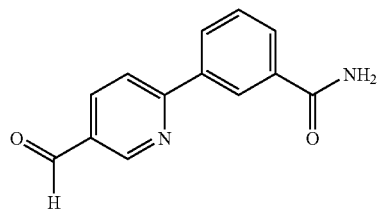

To a solution of 6-bromopyridine-3-carbaldehyde (1.41 g, 7.6 mmol) in toluene (25 mL) under argon, was added palladium tetrakistriphenylphosphine (0.88 g, 0.8 mmol) followed by 2M Na$_2$CO$_3$ (13 mL), (3-aminocarbonylbenzene)boronic acid (1.5 g, 9.1 mmol) and EtOH (13 mL). The mixture was heated to 75° C. for 16 h. After cooling, EtOAc (75 mL) and THF (75 mL) were added and the organics washed with water (3×50 mL), brine (50 mL) and dried (MgSO$_4$). The solvent was removed in vacuo and the residue purified by column chromatography (0.5% NH₃: 5% MeOH: DCM) to give the title compound: RT=2.53 min; m/z (ES⁺)=227.0 [M+H]⁺.

Preparation 13:
4-Fluoro-3-(5-formylpyridin-2-yl)benzamide

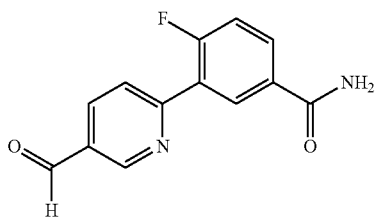

To a solution of 6-bromo-3-pyridinecarboxaldehyde (336 mg, 1.80 mmol) in DME (8 mL) and EtOH (4 mL) under argon, was added (5-carbamoyl-2-fluorophenyl)boronic acid (300 mg, 1.64 mmol) followed by palladium tetrakistriphenylphosphine (190 mg, 0.16 mmol) and 2M Na₂CO₃ (4 mL). The mixture was heated to 80° C. for 16 h and then allowed to cool to rt. The mixture was partitioned between EtOAc (50 mL), THF (50 mL) and Na₂CO₃ (20 mL). The aqueous was extracted with EtOAc (50 mL) and the combined organics washed with brine (30 mL) and dried (MgSO₄). The solvent was removed in vacuo and the residue purified by column chromatography (0.4% NH₃: 4% MeOH: DCM) to give the title compound: RT=2.50 min; m/z (ES⁺)=245.0 [M+H]⁺.

Preparation 14:
3-(5-Formyl-3-methylpyridin-2-yl)benzamide

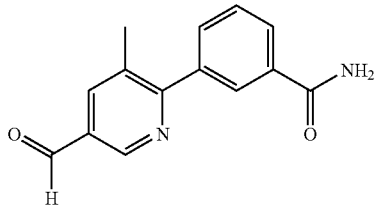

To a solution of 2,5-dibromo-3-methylpyridine (2.5 g, 10.0 mmol) in toluene (120 mL) and TMEDA (1.95 mL, 13 mmol) at −78° C. under argon was added 2.5M n-BuLi in hexanes (4.9 mL, 12 mmol) dropwise. The mixture was stirred at −78° C. for 2 h then DMF (1 mL, 13 mmol) was added. After 45 min AcOH (10 mL) was added and the mixture warmed to rt. EtOAc (60 mL) and 1N HCL (50 mL) were added and the mixture stirred for 16 h. The organic phase was separated and the aqueous phase washed with EtOAc (2×60 mL). The combined organic phases were washed with NaHCO₃ (50 mL), brine (100 mL) and dried (MgSO₄) and the solvent removed in vacuo. The residue was dissolved in methanol (50 mL) and stirred for 1 h. The solvent was removed in vacuo and the residue purified by column chromatography (15% EtOAc: iso-hexane) to give 2-bromo-5-dimethoxymethyl-3-methylpyridine. To 2-bromo-5-dimethoxymethyl-3-methylpyridine (2.61 g, 10.8 mmol) in DME (60 mL) and ethanol (40 mL) was added 3-carboxamidobenzene boronic acid (1.94 g, 12.9 mmol) and 2M Na₂CO₃ (40 mL). Argon was bubbled through the mixture for 15 min. Bis(triphenylphosphino)palladium dichloride (0.76 g, 1.1 mmol) was added and the reaction heated to 75° C. for 6.5 h. The reaction was cooled and the mixture partitioned between water (200 mL) and EtOAc (200 mL). The aqueous phase was extracted with EtOAc (2×50 mL) and the combined organics phases dried (MgSO₄). The solvent was removed in vacuo and the residue purified by column chromatography (0.5% NH₃: 3% MeOH: DCM to 0.5% NH₃: 5% MeOH: DCM) to give 3-(5-dimethoxymethyl-3-methylpyridin-2-yl)benzamide. To 3-(5-dimethoxymethyl-3-methylpyridin-2-yl)benzamide (2.2 g, 7.7 mmol) in DCM (25 mL) was added TFA (15 mL). After 10 min water (15 mL) was added and the mixture stirred for 64 h. The solvent was removed in vacuo and the residue partitioned between EtOAc (100 mL) and NaHCO₃ (50 mL). The organic phase was washed with water (50 mL), brine (50 mL) and dried (MgSO₄). The solvent was removed in vacuo to give the title compound: RT=2.42 min; m/z (ES⁺)=241.0 [M+H]⁺.

Preparation 15: (6-Bromopyridin-3-ylmethyl)-(2-cyclohexylethyl)amine

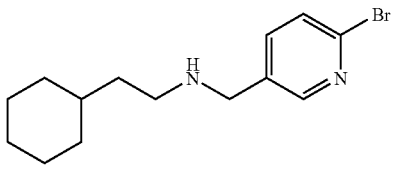

Using the procedure outlined in Example 60, 6-bromo-3-pyridinecarboxaldehyde and cyclohexylamine were converted to the title compound: RT=2.49 min; m/z (ES⁺)=297.0 [M+H]⁺.

Preparation 16: 4-Chloro-3-[5-[(2-cyclohexylethylamino)methyl]pyridin-2-yl]benzonitrile

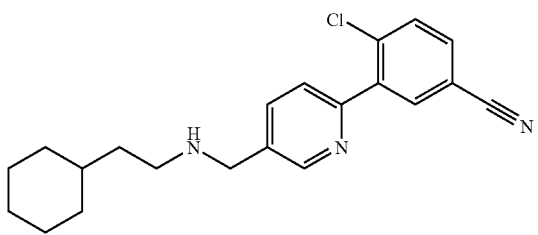

Using the procedure outlined in Preparation 13, (6-bromopyridin-3-ylmethyl)-(2-cyclohexylethyl)amine and 2-chloro-5-cyanophenyl boronic acid were converted to the title compound: RT=2.79 min; m/z (ES⁺)=354.1 [M+H]⁺.

Preparation 17: 3-Bromo-4-methylbenzamide

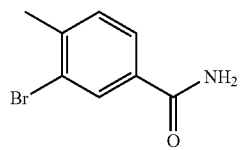

3-Bromo-4-methylbenzoic acid (1.5 g, 7.0 mmol) in thionyl chloride (10 mL) was heated to 80° C. for 1 h. The solvent was removed in vacuo and the residue was dissolved in DCM (16 mL) at 0° C. under argon before adding ammonium chloride (410 mg, 7.7 mmol) and Et$_3$N (2.43 mL, 17.4 mmol). The reaction was stirred at 0° C. for 15 min then allowed to warm to rt over 16 h. The solvent was removed in vacuo and the mixture partitioned between EtOAc (120 mL) and 1M NaOH (60 mL). The organic phase was washed with 1M NaOH (60 mL), brine (60 mL) and dried (MgSO$_4$). The solvent was removed in vacuo. Trituration with ether and then MeOH gave the title compound: RT=2.78 min; m/z (ES$^+$)=214.0 [M+H]$^+$.

Preparation 18: 4-Methyl-3-(4,4,5,5-tetramethyl-[1,3,2]dioxaborolan-2-yl)benzamide

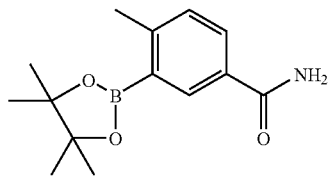

3-Bromo-4-methylbenzamide (300 mg, 1.4 mmol), bis(pinacolato)diboron (463 mg, 1.82 mmol), bis(diphenylphosphino)ferrocene palladium dichloride (114 mg, 0.14 mmol) and palladium acetate (481 mg, 4.91 mmol) were purged with argon for 10 min in a sealed tube. DMF (4.5 mL) was added and the mixture heated to 70° C. for 16 h. The mixture was cooled to rt and the solvent removed in vacuo. The residue was dissolved in EtOAc (100 mL), washed with water (3×60 mL), brine (60 mL) and dried (MgSO$_4$). Solvent was removed in vacuo and the residue purified by column chromatography (5% MeOH: DCM) to give, after trituration with ether/isohexane, the title compound: RT=3.16 min; m/z (ES$^+$)=262.1 [M+H]$^+$.

Example 1

4'-[(4-Methylcyclohexylamino)methyl]biphenyl-3-carboxylic acid amide

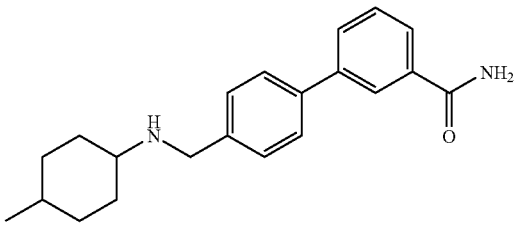

To a solution of 4'-formylbiphenyl-3-carboxylic acid amide (700 mg, 3.1 mmol) in methanol (15 mL) was added 4 Å molecular sieves (700 mg) and 4-methylcyclohexylamine (421 mg, 3.7 mmol). The mixture was stirred for 16 h before adding sodium borohydride (588 mg, 15.5 mmol). After 1 h water (10 mL) was added, the mixture was filtered through celite and the solvent removed in vacuo. Purification of the residue by column chromatography (0.5% NH$_3$: 6% MeOH: DCM) gave the title compound: RT=2.53 min; m/z (ES$^+$)= 323.0 [M+H]$^+$.

The procedure described in Example 1 was used to prepare Examples 2-33 from 4'-formylbiphenyl-3-carboxylic acid amide (Preparation 1) and the appropriate amine:

TABLE 1

| Ex | Structure | Name | RT (min) | m/z (ES$^+$) |
|---|---|---|---|---|
| 2 | 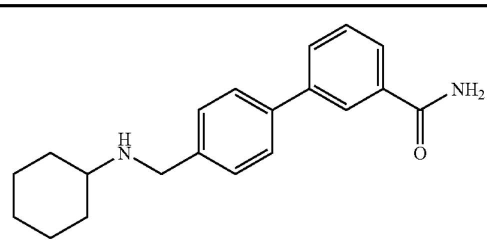 | 4'-Cyclohexylamino-methylbiphenyl-3-carboxylic acid amide | 2.34 | 309.1 [M + H]$^+$ |
| 3 | 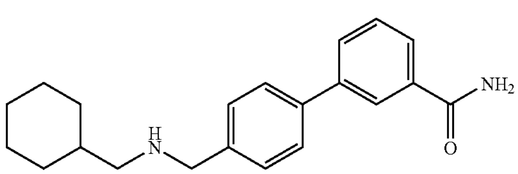 | 4'-[(Cyclohexylmethyl-amino)methyl]-biphenyl-3-carboxylic acid amide | 2.44 | 323.1 [M + H]$^+$ |
| 4 | 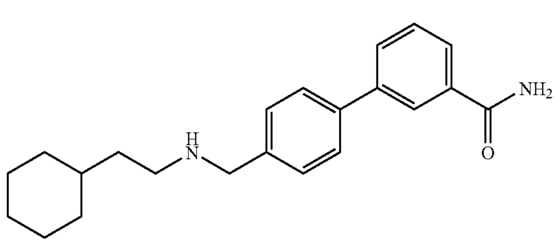 | 4'-[(2-Cyclohexyl-ethylamino)methyl]-biphenyl-3-carboxylic acid amide | 2.70 | 337.1 [M + H]$^+$ |

TABLE 1-continued

| Ex | Structure | Name | RT (min) | m/z (ES+) |
|---|---|---|---|---|
| 5 | 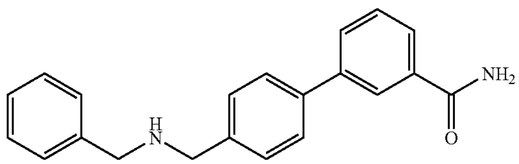 | 4'-(Benzylamino-methyl)biphenyl-3-carboxylic acid amide | 2.44 | 317.0 [M + H]+ |
| 6 | 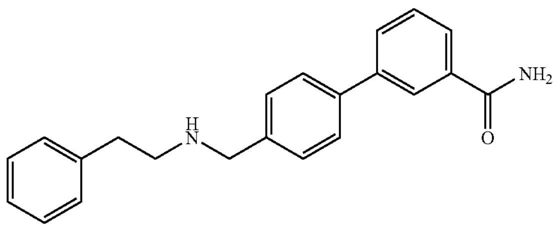 | 4'-(Phenethylamino-methyl)biphenyl-3-carboxylic acid amide | 2.42 | 331.1 [M + H]+ |
| 7 | 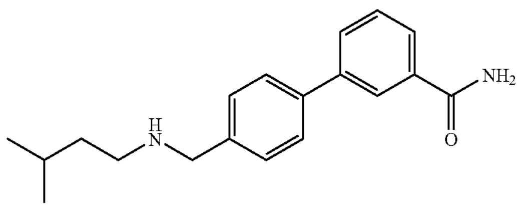 | 4'-[(3-Methyl-butylamino)methyl]-biphenyl-3-carboxylic acid amide | 2.32 | 297.1 [M + H]+ |
| 8 | 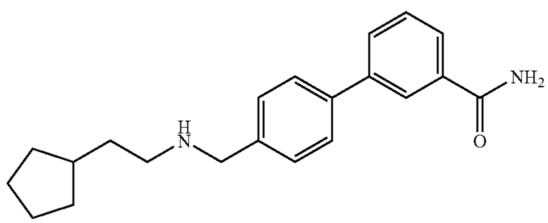 | 4'-[(2-Cyclopentyl-ethylamino)methyl]-biphenyl-3-carboxylic acid amide | 2.47 | 323.1 [M + H]+ |
| 9 | 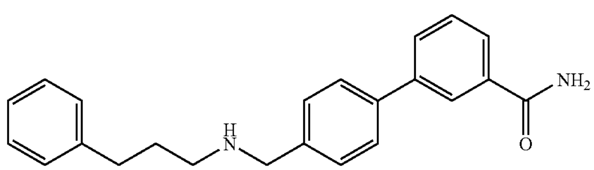 | 4'-[(3-Phenyl-propylamino)methyl]-biphenyl-3-carboxylic acid amide | 2.45 | 345.1 [M + H]+ |
| 10 | 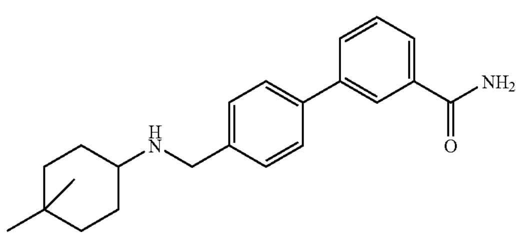 | 4'-[(4,4-Dimethyl-cyclohexylamino)-methyl]biphenyl-3-carboxylic acid amide | 2.57 | 337.1 [M + H]+ |
| 11 | 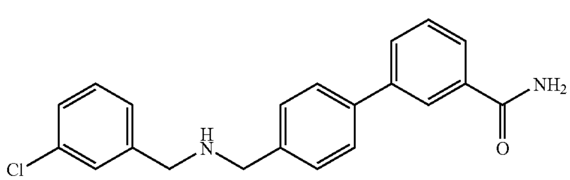 | 4'-[(3-Chlorobenzyl-amino)methyl]-biphenyl-3-carboxylic acid amide | 2.56 | 351.0 [M + H]+ |

TABLE 1-continued

| Ex | Structure | Name | RT (min) | m/z (ES+) |
|----|-----------|------|----------|-----------|
| 12 | 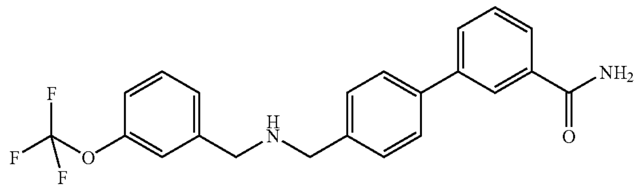 | 4'-[(3-Trifluoro-methoxybenzylamino)-methyl]biphenyl-3-carboxylic acid amide | 2.62 | 401.0 [M + H]+ |
| 13 | 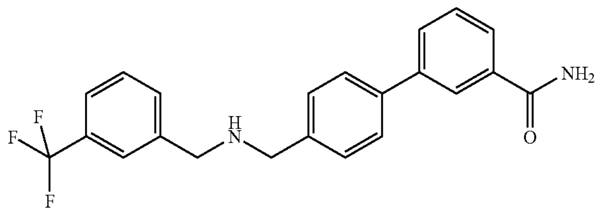 | 4'-[(3-Trifluoromethyl-benzylamino)methyl]-biphenyl-3-carboxylic acid amide | 2.55 | 385.0 [M + H]+ |
| 14 | 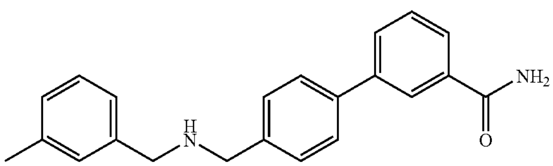 | 4'-[(3-Methyl-benzylamino)methyl]biphenyl-3-carboxylic acid amide | 2.55 | 331.1 [M + H]+ |
| 15 | 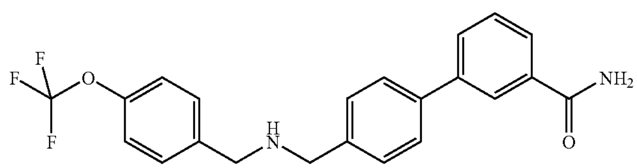 | 4'-[(4-Trifluoro-methoxybenzylamino)-methyl]biphenyl-3-carboxylic acid amide | 2.73 | 401.0 [M + H]+ |
| 16 | 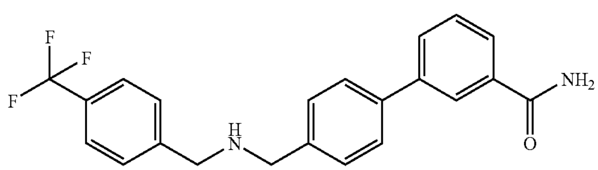 | 4'-[(4-Trifluoromethyl-benzylamino)methyl]-biphenyl-3-carboxylic acid amide | 2.56 | 385.1 [M + H]+ |
| 17 | 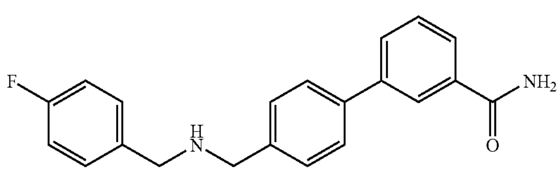 | 4'-[(4-Fluorobenzyl-amino)methyl]-biphenyl-3-carboxylic acid amide | 2.49 | 335.0 [M + H]+ |
| 18 | 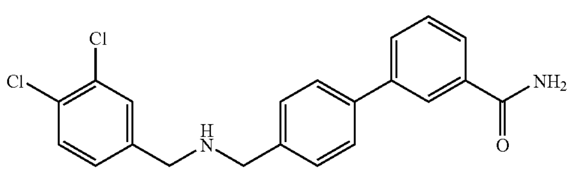 | 4'-[(3,4-Dichloro-benzylamino)methyl]-biphenyl-3-carboxylic acid amide | 2.59 | 385.0 [M + H]+ |
| 19 | 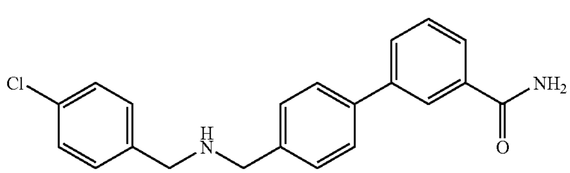 | 4'-[(4-Chlorobenzyl-amino)methyl]-biphenyl-3-carboxylic acid amide | 2.47 | 351.0 [M + H]+ |

TABLE 1-continued

| Ex | Structure | Name | RT (min) | m/z (ES+) |
|---|---|---|---|---|
| 20 | 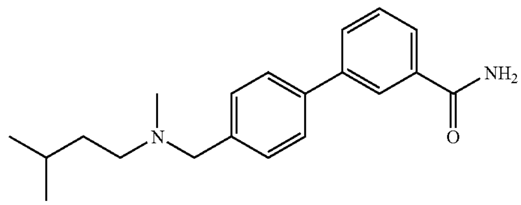 | 4'-{[Methyl-(3-methyl-butyl)amino]methyl}-biphenyl-3-carboxylic acid amide | 3.36* | 311.3 [M + H]+ |
| 21 | 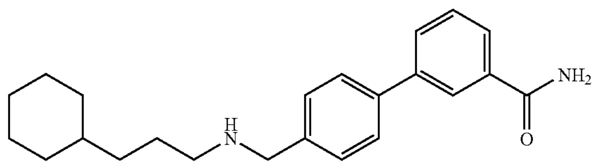 | 4'-[(3-Cyclohexyl-propylamino)methyl]-biphenyl-3-carboxylic acid amide | 3.85* | 351.3 [M + H]+ |
| 22 | 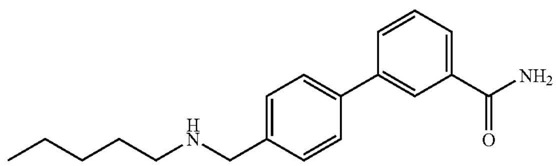 | 4'-Pentylaminomethyl-biphenyl-3-carboxylic acid amide | 2.96* | 297.2 [M + H]+ |
| 23 | 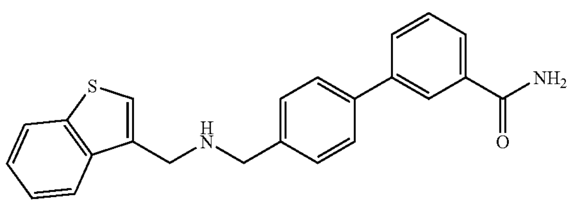 | 4'-{[(Benzo[b]-thiophen-3-ylmethyl)-amino]methyl}-biphenyl-3-carboxylic acid amide | 3.14* | 373.1 [M + H]+ |
| 24 | 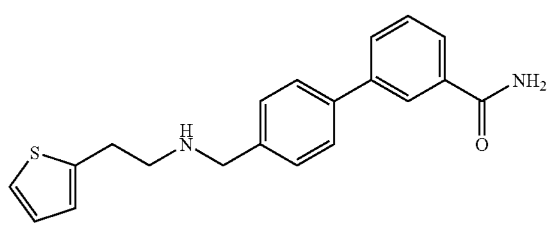 | 4'-[(2-Thiophe-2-yl-ethylamino)methyl]-biphenyl-3-carboxylic acid amide | 2.76* | 337.2 [M + H]+ |
| 25 | 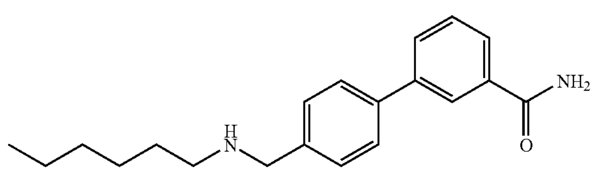 | 4-Hexylaminomethyl-biphenyl-3-carboxylic acid amide | 3.24* | 311.2 [M + H]+ |
| 26 | 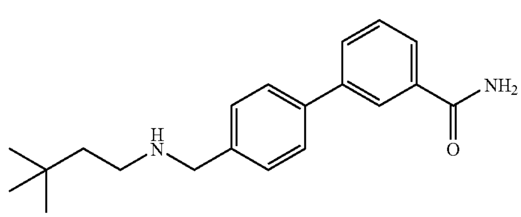 | 4'-[3,3-Dimethyl-butylamino)methyl]-biphenyl-3-carboxylic acid amide | 3.10* | 311.3 [M + H]+ |

TABLE 1-continued

| Ex | Structure | Name | RT (min) | m/z (ES+) |
|---|---|---|---|---|
| 27 | 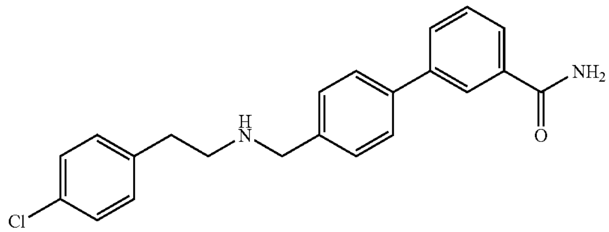 | 4'-{[2-(4-Chloro-phenyl)ethylamino]-methyl}biphenyl-3-carboxylic acid amide | 3.10* | 365.2 [M + H]+ |
| 28 | 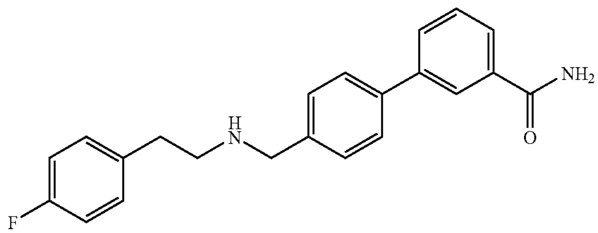 | 4'-{[2-(4-Fluoro-phenyl)ethylamino]-methyl}biphenyl-3-carboxylic acid amide | 2.88* | 349.2 [M + H]+ |
| 29 | 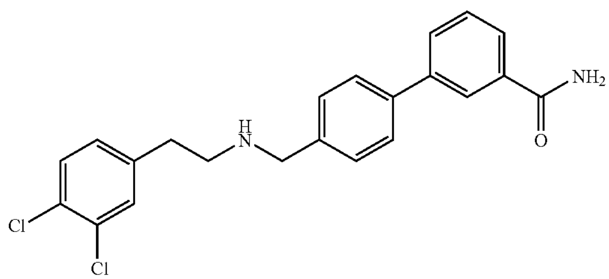 | 4'-{[2-(3,4-Dichloro-phenyl)ethylamino]-methyl}biphenyl-3-carboxylic acid amide | 3.32* | 399.1, 401.1 [M + H]+ |
| 30 | 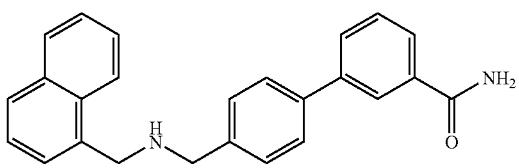 | 4'-{[(Naphthalen-1-ylmethyl)amino]-methyl}biphenyl-3-carboxylic acid amide | 3.44* | 367.2 [M + H]+ |
| 31 | 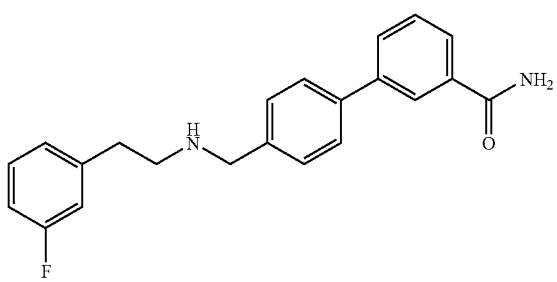 | 4'-{[2-(3-Fluoro-phenyl)ethylamino]-methyl}biphenyl-3-carboxylic acid amide | 3.13* | 349.1 [M + H]+ |
| 32 | 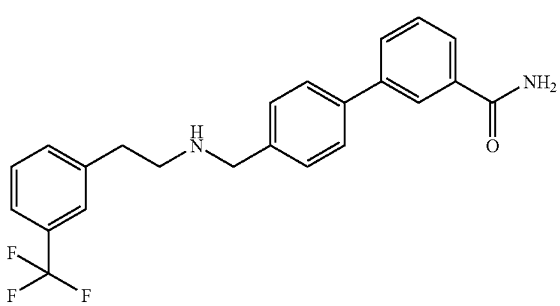 | 4'-{[2-(3-Trifluoro-methylphenyl)ethyl-amino]methyl}-biphenyl-3-carboxylic acid amide | 3.45* | 399.1 [M + H]+ |

TABLE 1-continued

| Ex | Structure | Name | RT (min) | m/z (ES+) |
|---|---|---|---|---|
| 33 | 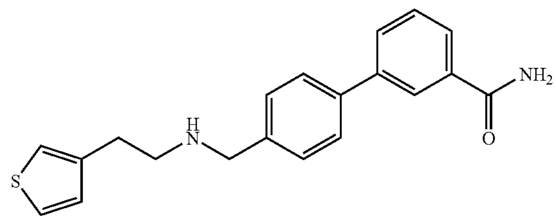 | 4'-[(2-Thiophen-3-yl-ethylamino)methyl]-biphenyl-3-carboxylic acid amide | 2.94* | 337.1 [M + H]+ |

*LCMS method 2

Example 34

4'-{[2-(4,4-Difluorocyclohexyl)ethylamino]methyl}biphenyl-3-carboxylic acid amide

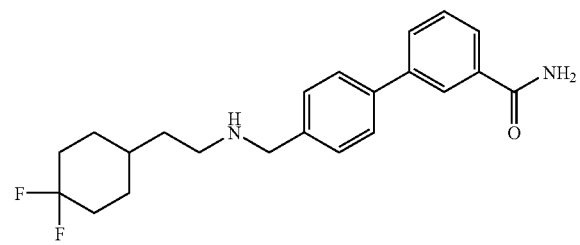

To a solution of 4'-formylbiphenyl-3-carboxylic acid amide (Preparation 1, 200 mg, 0.89 mmol) in methanol (4 mL) was added 2-(1,4-dioxaspiro[4.5]dec-8-yl)ethylamine (181 mg, 0.98 mmol). The mixture was stirred for 16 h under argon before adding sodium borohydride (40 mg, 1.07 mmol). After 1 h water (0.5 mL) was added and the solvent was removed in vacuo. The residue was subjected to column chromatography (0.5% NH$_3$: 5% MeOH: DCM) and gave an inseparable mixture of 4'-{[2-(1,4-dioxaspiro[4.5]dec-8-yl)ethylamino]methyl}biphenyl-3-carboxylic acid amide and 4'-{[2-(4-oxocyclohexyl)ethylamino]methyl}biphenyl-3-carboxylic acid amide. This crude mixture was dissolved in acetone (10 mL), 2M HCl (5 mL) was added and the mixture stirred for 64 h at rt. The solvent was removed in vacuo and then the mixture diluted with water (50 mL) and extracted with EtOAc (2×40 mL). The combined organics were washed with water (15 mL), the aqueous fractions were combined and basified to pH 14 by addition of 2M NaOH. The aqueous was extracted with EtOAc (3×30 mL), the combined organics washed with brine (20 mL) and dried (MgSO$_4$). Solvent was removed in vacuo to give 4'-{[2-(4-oxo-cyclohexyl)ethylamino]methyl}biphenyl-3-carboxylic acid amide.

To a solution of 4'-{[2-(4-oxocyclohexyl)ethylamino]methyl}biphenyl-3-carboxylic acid amide (50 mg, 0.14 mmol) in DCM (5 mL) under argon was added DAST (187 uL, 1.4 mmol). After 4 h saturated NaHCO$_3$ (20 mL) was added followed by DCM (30 mL), the mixture was stirred vigorously for 15 min. The layers were separated, the aqueous extracted with DCM (3×20 mL) and the combined organics were washed with brine and dried (MgSO$_4$). The solvent was removed in vacuo and the residue purified by column chromatography (0.5% NH$_3$: 5% MeOH: DCM) to give the title compound: RT=2.52 min; m/z (ES+)=373.1 [M+H]+.

The procedure described in Example 1 was used to prepare Examples 35-38 from 3'-fluoro-4'-formylbiphenyl-3-carboxylic acid amide (Preparation 7) or 3'-chloro-4'-formylbiphenyl-3-carboxylic acid amide (Preparation 6) and the appropriate amine:

TABLE 2

| Ex | Structure | Name | RT (min) | m/z (ES) |
|---|---|---|---|---|
| 35 | 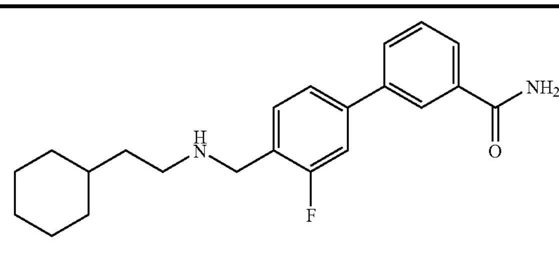 | 4'-[(2-Cyclohexyl-ethylamino)methyl]-3'-fluorobiphenyl-3-carboxylic acid amide | 2.76 | 355.3 [M + H]+ |
| 36 | 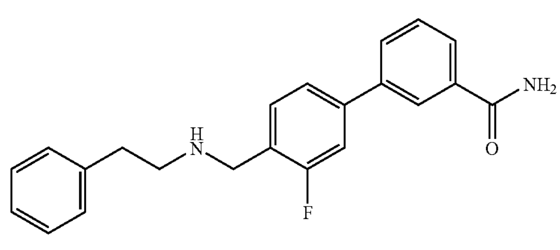 | 3'-Fluoro-4'-(phenethyl-aminomethyl)-biphenyl-3-carboxylic acid amide | 2.49 | 349.0 [M + H]+ |

TABLE 2-continued

| Ex | Structure | Name | RT (min) | m/z (ES) |
|---|---|---|---|---|
| 37 | 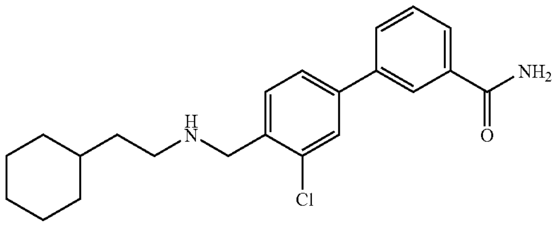 | 3'-Chloro-4'-[(2-cyclohexylethyl-ammino)methyl]-biphenyl-3-carboxylic acid amide | 2.69 | 371.0 [M + H]$^+$ |
| 38 | 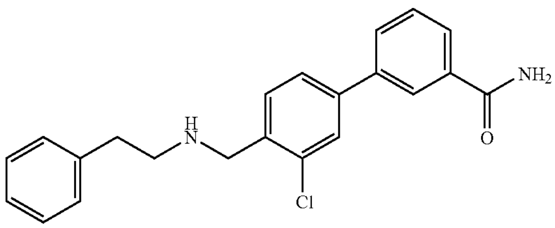 | 3'-Chloro-4'-(phenethylamino methyl)biphenyl-3-carboxylic acid amide | 2.52 | 365.0 [M + H]$^+$ |

The procedure described in Example 1 was used to prepare Examples 39-42 from 3-(6-formylpyridin-3-yl)benzamide (Preparation 8) and the appropriate amine:

TABLE 3

| Ex | Structure | Name | RT (min) | m/z (ES$^+$) |
|---|---|---|---|---|
| 39 | 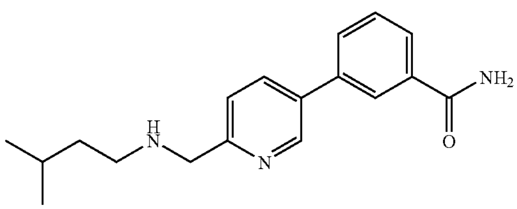 | 3-{6-[(3-Methyl-butylamino)methyl]-pyridin-3-yl}benzamide | 2.26 | 298.1 [M + H]$^+$ |
| 40 | 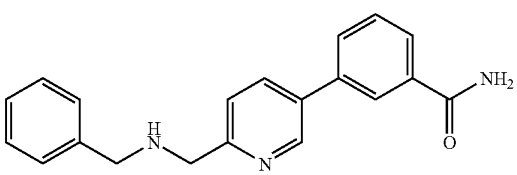 | 3-[6-(Benzylamino-methyl)pyridin-3-yl]-benzamide | 2.24 | 318.1 [M + H]$^+$ |
| 41 | 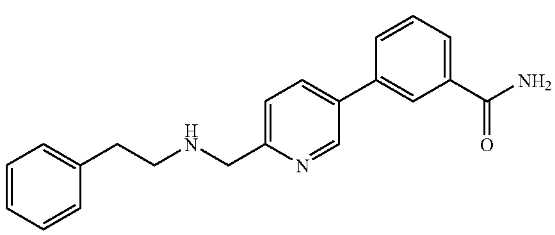 | 3-[6-(Phenethylamino-methyl)pyridin-3-yl]-benzamide | 2.31 | 332.1 [M + H]$^+$ |
| 42 | 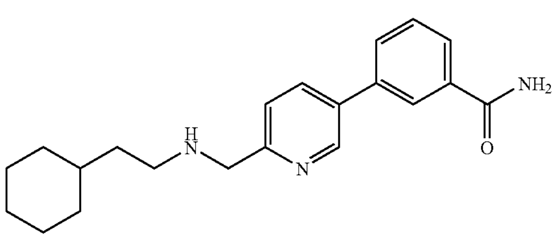 | 3-{6-[(2-Cyclohexyl-ethylamino)methyl]-pyridin-3-yl}benzamide | 2.52 | 338.1 [M + H]$^+$ |

The procedure described in Example 1 was used to prepare Examples 43-45 from 2'-fluoro-4'-formylbiphenyl-3-carboxylic acid amide (Preparation 9) and the appropriate amine:

TABLE 4

| Ex | Structure | Name | RT (min) | m/z (ES+) |
|---|---|---|---|---|
| 43 | 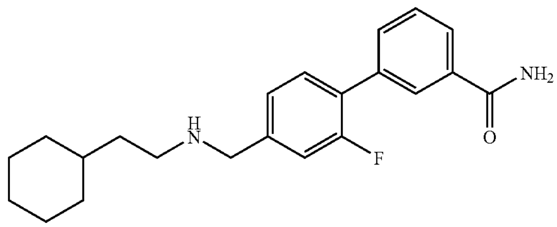 | 4'-[(2-Cyclohexylethylamino)methyl]-2'-fluorobiphenyl-3-carboxylic acid amide | 2.65 | 355.3 [M + H]+ |
| 44 | 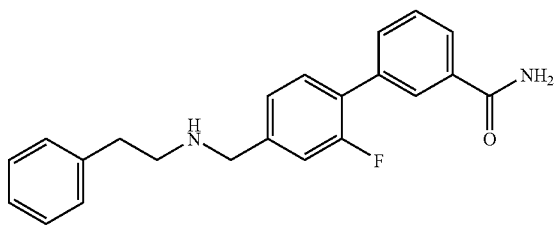 | 2'-Fluoro-4'-(phenethylaminomethyl)biphenyl-3-carboxylic acid amide | 2.36 | 349.2 [M + H]+ |
| 45 | 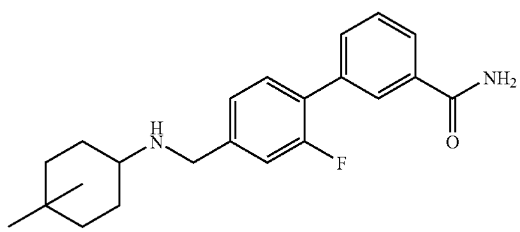 | 4'-[(4,4-Dimethylcyclohexylamino)methyl]-2'-fluorobiphenyl-3-carboxylic acid amide | 2.62 | 355.0 [M + H]+ |

The procedure described in Example 1 was used to prepare Examples 46-53 from 4'-formyl-2'-methylbiphenyl-3-carboxylic acid amide (Preparation 10) and the appropriate amine:

TABLE 5

| Ex | Structure | Name | RT (min) | m/z (ES+) |
|---|---|---|---|---|
| 46 | 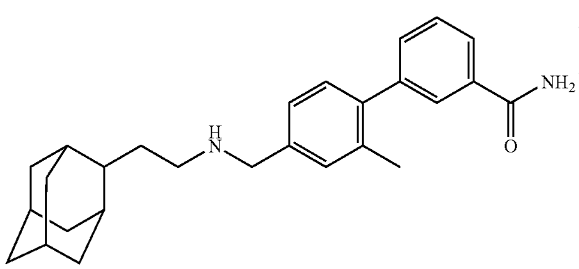 | 4'-[(2-Adamantan-2-ylethylamino)methyl]-2'-methylbiphenyl-3-carboxylic acid amide | 2.95 | 403.0 [M + H]+ |
| 47 | 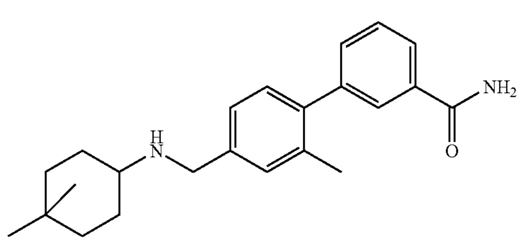 | 4'-[(4,4-Dimethylcyclohexylamino)methyl]-2'-methylbiphenyl-3-carboxylic acid amide | 2.67 | 351.0 [M + H]+ |

TABLE 5-continued

| Ex | Structure | Name | RT (min) | m/z (ES+) |
|---|---|---|---|---|
| 48 | 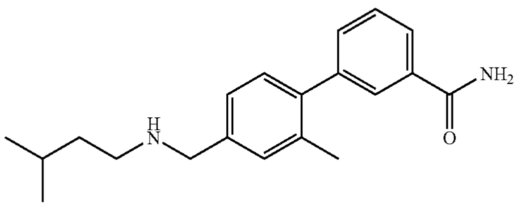 | 2'-Methyl-4'-[(3-methylbutylamino)-methyl]biphenyl-3-carboxylic acid amide | 2.36 | 311.0 [M + H]+ |
| 49 | 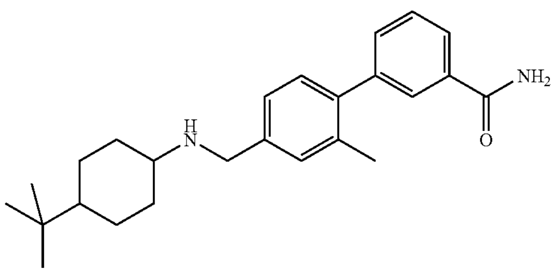 | 4'-[(4-tert-Butyl-cyclohexylamino)-methyl]-2'-methyl-biphenyl-3-carboxylic acid amide | 2.79 | 379.0 [M + H]+ |
| 50 | 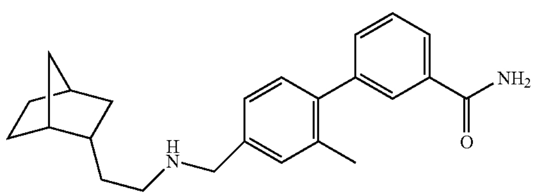 | 4'-[(2-Bicyclo[2.2.1]-hept-2-yl-ethylamino)-methyl]-2'-methyl-biphenyl-3-carboxylic acid amide | 2.72 | 379.0 [M + H]+ |
| 51 | 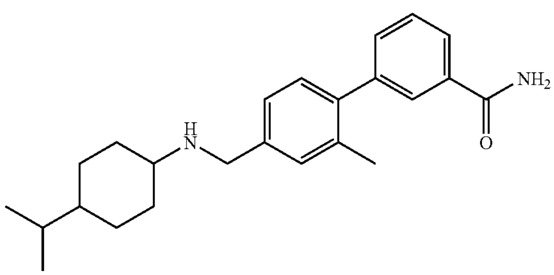 | 4'-[(4-Isopropyl-cyclohexylamino)-methyl]-2'-methyl-biphenyl-3-carboxylic acid amide | 2.82 | 365.0 [M + H]+ |
| 52 | 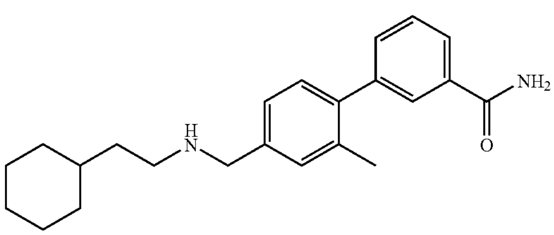 | 4'-[(2-Cyclohexyl-ethylamino)methyl]-2'-methylbiphenyl-3-carboxylic acid amide | 2.61 | 351.3 [M + H]+ |
| 53 | 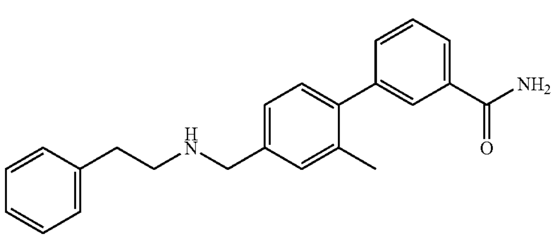 | 2'-Methyl-4'-(phenethylamino-methyl)biphenyl-3-carboxylic acid amide | 2.50 | 345.2 [M + H]+ |

The procedure described in Example 1 was used to prepare Examples 54 and 55 from 4'-formyl-3'-methylbiphenyl-3-carboxylic acid amide (Preparation 11) and the appropriate amine:

TABLE 6

| Ex | Structure | Name | RT (min) | m/z (ES+) |
|---|---|---|---|---|
| 54 | 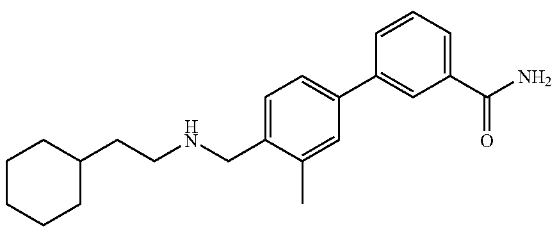 | 4'-[(2-Cyclohexyl-ethylamino)methyl]-3'-methylbiphenyl-3-carboxylic acid amide | 2.62 | 345.0 [M + H]+ |
| 55 | 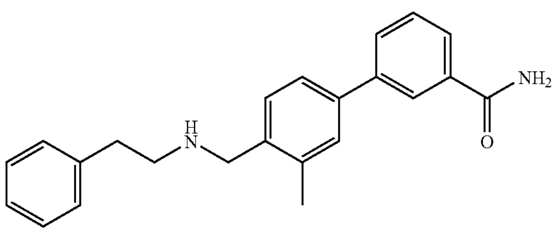 | 3'-Methyl-4'-(phenethylamino-methyl)biphenyl-3-carboxylic acid amide | 2.68 | 351.3 [M + H]+ |

Example 56 cis-4'-[(4-tert-Butylcyclohexylamino)methyl]-2'-fluorobiphenyl-3-carboxylic acid amide

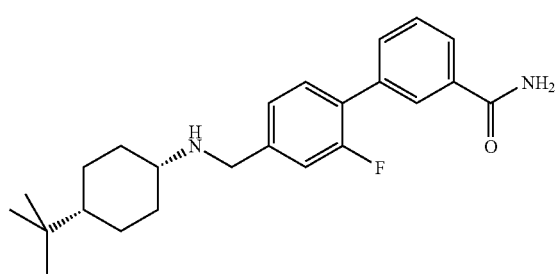

Example 57 trans-4'-[(4-tert-Butylcyclohexylamino)methyl]-2'-fluorobiphenyl-3-carboxylic acid amide

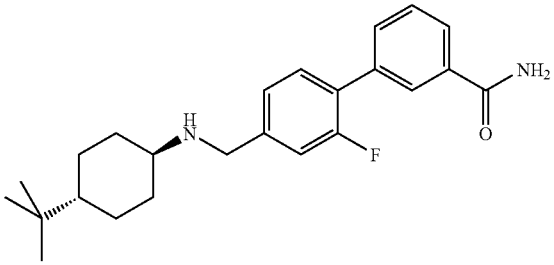

To a suspension of 2'-fluoro-4'-formylbiphenyl-3-carboxylic acid amide (Preparation 9, 252 mg, 1.0 mmol) in DCM (100 mL) was added 4-tert-butylcyclohexylamine (500 µL, 3.2 mmol), acetic acid (200 µL, 3.5 mmol) and sodium triacetoxyborohydride (648 mg, 3.1 mmol). The mixture was stirred at rt for 16 h. EtOAc (100 mL) was added and the organics washed with aqueous NaHCO₃ (30 mL), brine (30 mL) and dried (MgSO₄). The solvent was removed in vacuo and the residue purified by column chromatography (17% EtOH: Toluene) to give cis-4'-[(4-tert-butylcyclohexylamino)methyl]-2'-fluorobiphenyl-3-carboxylic acid amide: RT=2.84 min; m/z (ES+)=383.0 [M+H]+, and trans-4'-[(4-tert-butylcyclohexylamino)methyl]-2'-fluorobiphenyl-3-carboxylic acid amide: RT=2.87 min; m/z (ES+)=383.0 [M+H]+.

The procedure described in Example 56/57 was used to prepare Examples 58 and 59 from 4'-formylbiphenyl-3-carboxylic acid amide (Preparation 1) and the appropriate amine:

TABLE 7

| Ex | Structure | Name | RT (min) | m/z (ES+) |
|---|---|---|---|---|
| 58 | 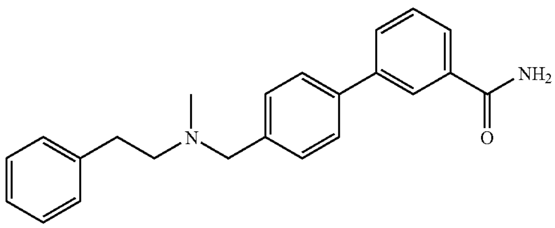 | 4'-[(Methylphenethyl-amino)methyl]-biphenyl-3-carboxylic acid amide | 2.36 | 345.1 [M + H]+ |
| 59 | 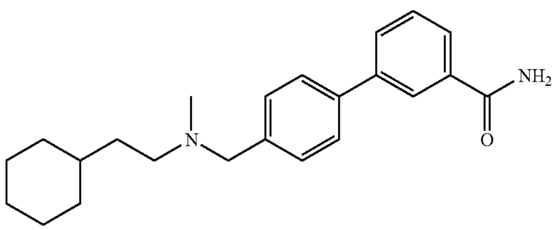 | 4'-{[(2-Cyclohexyl-ethyl)methylamino]-methyl}biphenyl-3-carboxylic acid amide | 2.66 | 351.1 [M + H]+ |

Example 60

3-[5-(Phenethylaminomethyl)pyridin-2-yl]benzamide

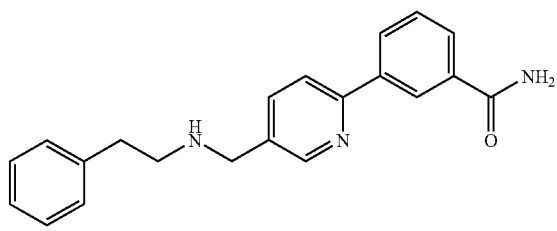

To a solution of 3-(5-formylpyridin-2-yl)benzamide (40 mg, 0.18 mmol) in MeOH (2.5 mL) was added phenethylamine (27 μL, 0.21 mmol). The mixture was stirred for 16 h before adding sodium borohydride (33 mg, 0.88 mmol). After 16 h water (1 mL) was added and the solvent removed in vacuo. Purification of the residue by column chromatography (0.5% $NH_3$: 5% MeOH:DCM) gave the title compound: RT=2.32 min; m/z (ES+)=332.1 [M+H]+.

The procedure described in Example 60 was used to prepare Examples 61-72 from 3-(5-formylpyridin-2-yl)benzamide (Preparation 12) and the appropriate amine:

TABLE 8

| Ex | Structure | Name | RT (min) | m/z (ES+) |
|---|---|---|---|---|
| 61 | 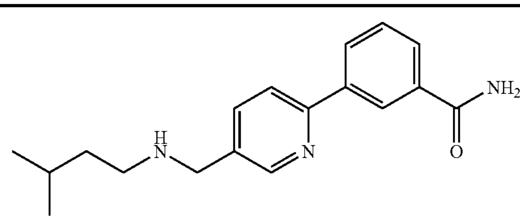 | 3-{5-[(3-Methyl-butylamino)methyl]-pyridin-2-yl}benzamide | 2.22 | 298.1 [M + H]+ |
| 62 | 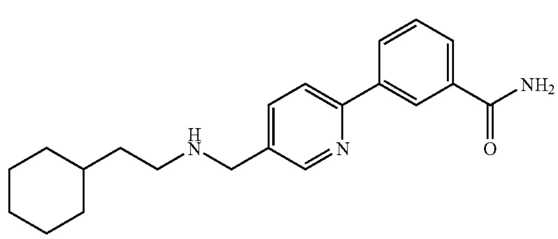 | 3-{5-[(2-Cyclohexyl-ethylamino)methyl]-pyridin-2-yl}benzamide | 2.52 | 338.1 [M + H]+ |

TABLE 8-continued

| Ex | Structure | Name | RT (min) | m/z (ES⁺) |
|---|---|---|---|---|
| 63 | 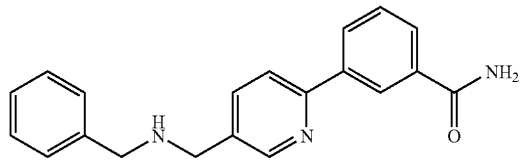 | 3-[5-(Benzylamino-methyl)pyridin-2-yl]-benzamide | 2.27 | 318.1 [M + H]⁺ |
| 64 | 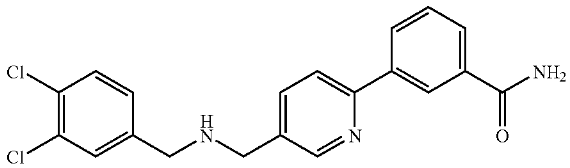 | 3-{5-[(3,4-Dichloro-benzylamino)methyl]-pyridin-2-yl}benzamide | 2.42 | 385.9 [M + H]⁺ |
| 65 | 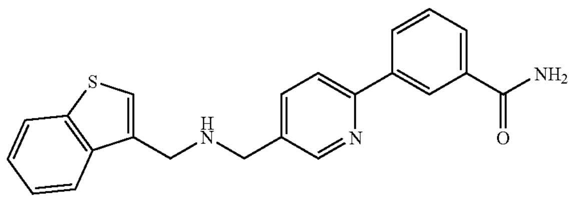 | 3-(5-{[(Benzo[b]-thiophen-3-ylmethyl)-amino]methyl}pyridin-2-yl)benzamide | 2.59 | 374.0 [M + H]⁺ |
| 66 | 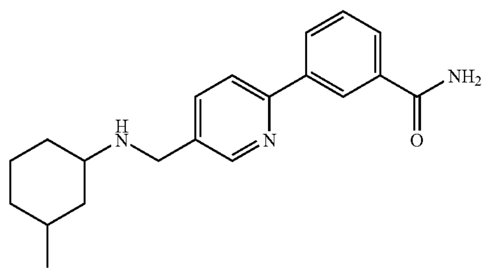 | 3-{5-[(3-Methylcyclo-hexylamino)methyl]-pyridin-2-yl}benzamide | 2.29 | 324.0 [M + H]⁺ |
| 67 | 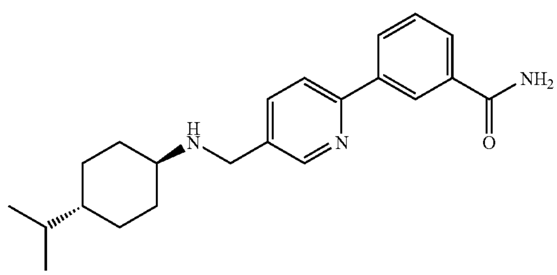 | trans-3-{5-[(4-Isopropylcyclohexyl-amino)methyl]-pyridin-2-yl}benzamide | 2.59 | 352.0 [M + H]⁺ |
| 68 | 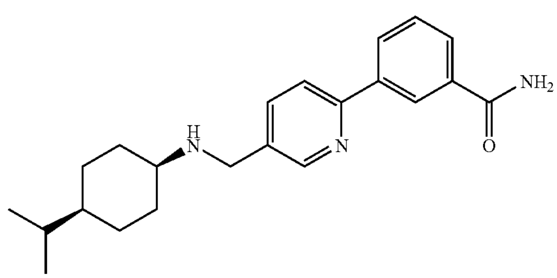 | cis-3-{5-[(4-Isopropyl-cyclohexylamino)-methyl]pyridin-2-yl}-benzamide | 2.63 | 352.0 [M + H]⁺ |
| 69 | 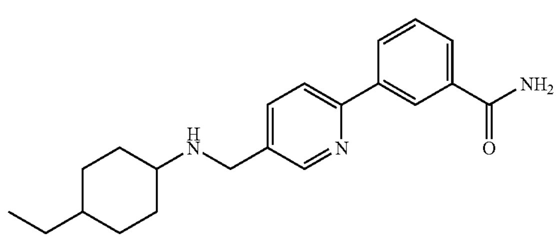 | 3-{5-[(4-Ethylcyclo-hexylamino)methyl]-pyridin-2-yl}benzamide | 2.50 | 338.0 [M + H]⁺ |

TABLE 8-continued

| Ex | Structure | Name | RT (min) | m/z (ES+) |
|---|---|---|---|---|
| 70 | 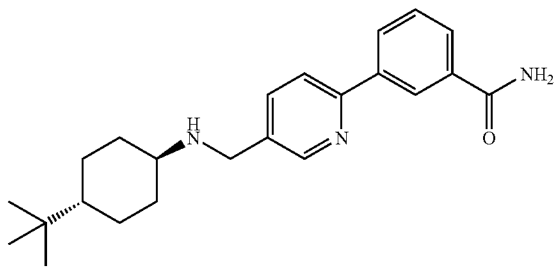 | trans-3-{5-[(4-tert-Butylcyclohexyl-amino)methyl]pyridin-2-yl}benzamide | 2.70 | 366.0 [M + H]+ |
| 71 | 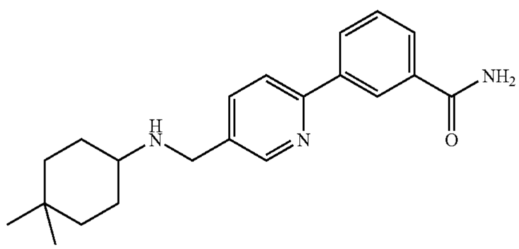 | 3-{5-[(4,4-Dimethyl-cyclohexylamino)-methyl]pyridin-2-yl}-benzamide | 2.44 | 338.0 [M + H]+ |
| 72 | 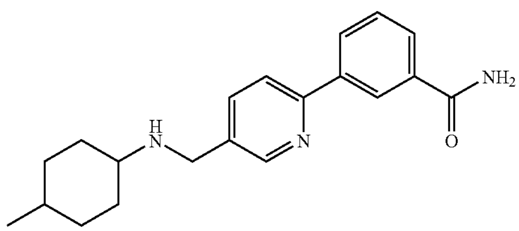 | 3-{5-[(4-Methylcyclo-hexylamino)methyl]-pyridin-2-yl}benzamide | 2.33 | 324.0 [M + H]+ |

Example 73

4-Fluoro-3-[5-(phenethylaminomethyl)pyridin-2-yl]benzamide

Using the method outlined in Example 60, 4-fluoro-3-(5-formylpyridin-2-yl)benzamide (Preparation 13) and phenethylamine were converted to the title compound: RT=2.30 min; m/z (ES+)=350.0 [M+H]+.

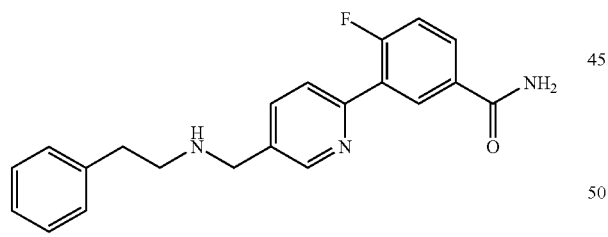

The procedure described in Example 60 was used to prepare Examples 74-79 from 3-(5-formyl-3-methylpyridin-2-yl)benzamide (Preparation 14) and the appropriate amine:

TABLE 9

| Ex | Structure | Name | RT (min) | m/z (ES+) |
|---|---|---|---|---|
| 74 | 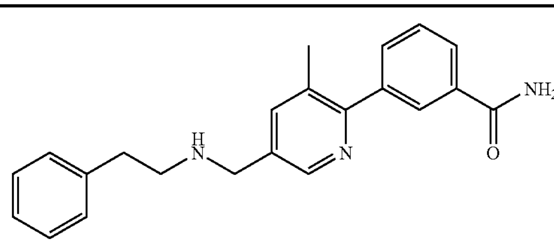 | 3-[3-Methyl-5-(phenethylamino-methyl)pyridin-2-yl]-benzamide | 2.17 | 346.0 [M + H]+ |

TABLE 9-continued

| Ex | Structure | Name | RT (min) | m/z (ES+) |
|---|---|---|---|---|
| 75 | 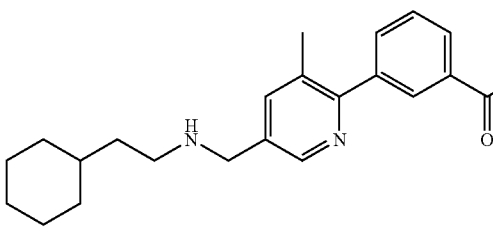 | 3-{5-[(2-Cyclohexyl-ethylamino)methyl]-3-methylpyridin-2-yl}-benzamide | 2.45 | 352.0 [M + H]+ |
| 76 | 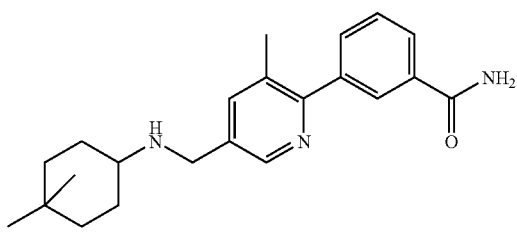 | 3-{5-[(4,4-Dimethyl-cyclohexylamino)-methyl]-3-methyl-pyridin-2-yl}benzamide | 2.29 | 352.0 [M + H]+ |
| 77 | 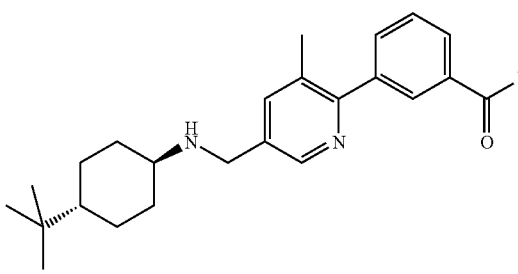 | Trans-3-{5-[(4-tert-Butylcyclohexyl-amino)methyl]-3-methylpyridin-2-yl}-benzamide | 2.56 | 380.1 [M + H]+ |
| 78 | 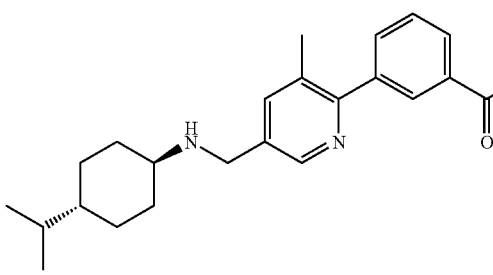 | 3-{5-[(4-Isopropyl-cyclohexylamino)-methyl]-3-methyl-pyridin-2-yl}benzamide | 2.45 | 366.0 [M + H]+ |
| 79 | 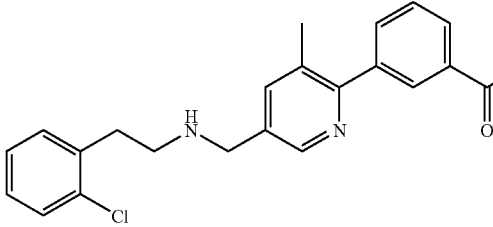 | 3-(5-{[2-(2-Chloro-phenyl)ethylamino]-methyl}-3-methyl-pyridin-2-yl)benzamide | 2.20 | 379.9 [M + H]+ |

Example 80

3-{5-[(2-Bicyclo[2.2.1]hept-2-ylethylamino)methyl]pyridin-2-yl}benzamide

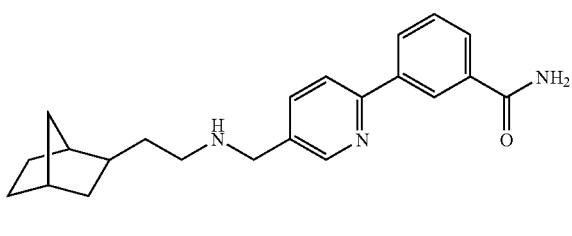

To a suspension of 3-(5-formylpyridin-2-yl)benzamide (Preparation 12, 108 mg, 0.48 mmol) in DCM (75 mL) was added 2-bicyclo[2.2.1]hept-2-ylethylamine (333 mg, 2.39 mmol), AcOH (80 μL, 1.4 mmol) and sodium triacetoxyborohydride (302 mg, 1.42 mmol). The mixture was stirred at rt for 16 h. EtOAc (100 mL) was added and the organic phase washed with aqueous NaHCO$_3$ (30 mL), brine (30 mL) and dried (MgSO$_4$). The solvent was removed in vacuo and the residue purified by column chromatography (10% MeOH: DCM to 20% MeOH: DCM) to give the title compound: RT=2.62 min; m/z (ES$^+$)=350.0 [M+H]$^+$.

The procedure described in Example 80 was used to prepare Examples 81-89 from 3-(5-formylpyridin-2-yl)benzamide (Preparation 12) or 3-(5-formyl-3-methylpyridin-2-yl)benzamide (Preparation 14) and the appropriate amine:

TABLE 10

| Ex | Structure | Name | RT (min) | m/z (ES$^+$) |
|---|---|---|---|---|
| 81 | 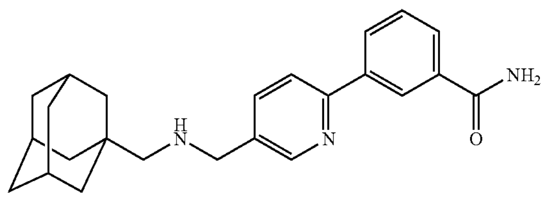 | 3-(5-{[Adamantan-1-ylmethylamino]-methyl}pyridin-2-yl)-benzamide | 2.67 | 376.1 [M + H]$^+$ |
| 82 | 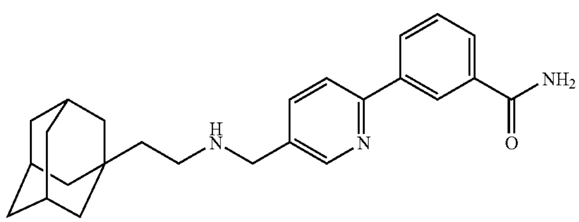 | 3-{5-[(2-Adamantan-1-ylethylamino)methyl]-pyridin-2-yl}benzamide | 2.72 | 390.2 [M + H]$^+$ |
| 83 | 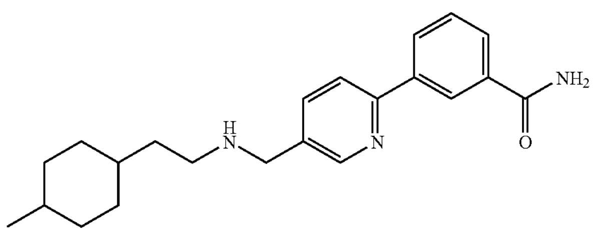 | 3-(5-{[2-(4-Methyl-cyclohexyl)ethyl-amino]methyl}pyridin-2-yl)benzamide | 2.69 | 352.2 [M + H]$^+$ |
| 84 | 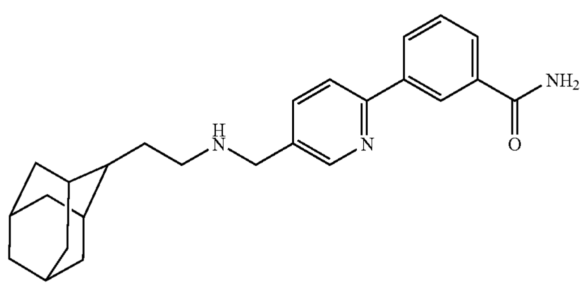 | 3-{5-[(2-Adamantan-2-ylethylamino)methyl]-pyridin-2-yl}benzamide | 2.70 | 390.1 [M + H]$^+$ |
| 85 | 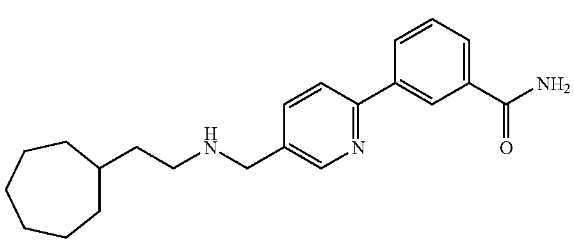 | 3-{5-[(2-Cycloheptyl-ethylamino)methyl]-pyridin-2-yl}benzamide | 2.56 | 352.1 [M + H]$^+$ |

TABLE 10-continued

| Ex | Structure | Name | RT (min) | m/z (ES+) |
|---|---|---|---|---|
| 86 | 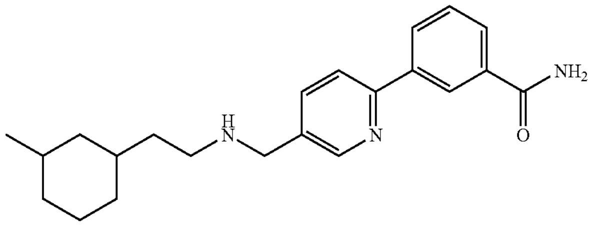 | 3-(5-{[2-(3-Methyl-cyclohexyl)ethyl-amino]methyl}pyridin-2-yl)benzamide | 2.62 | 352.0 [M + H]+ |
| 87 | 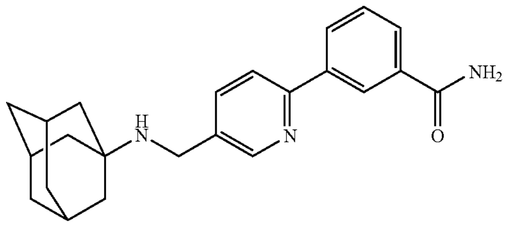 | 3-[5-(Adamantan-1-ylaminomethyl)-pyridin-2-yl]benzamide | 2.37 | 362.1 [M + H]+ |
| 88 | 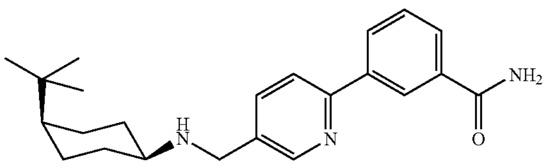 | Cis-3-{5-[(4-tert-Butyl-cyclohexylamino)-methyl]pyridin-2-yl}-benzamide | 2.66 | 366.3 [M + H]+ |
| 89 | 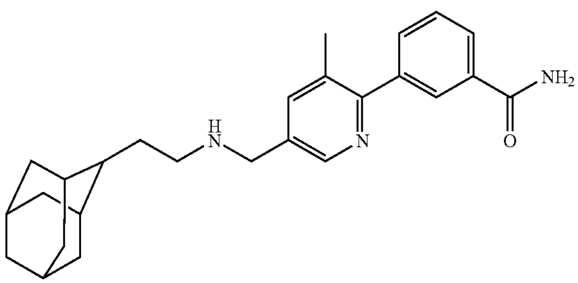 | 3-{5-[(2-Adamantan-2-ylethylamino)methyl]-3-methylpyridin-2-yl}-benzamide | 2.77 | 404.0 [M + H]+ |

Example 90

4-Chloro-3-{5-[(2-cyclohexylethylamino)methyl]pyridin-2-yl}benzamide

To a solution of 4-chloro-3-{5-[(2-cyclohexylethylamino)methyl]pyridin-2-yl}benzonitrile (170 mg, 0.48 mmol) in DMSO (4 mL) was added K₂CO₃ (66 mg, 0.48 mmol) and 70% hydrogen peroxide (0.5 mL, 4.8 mmol). The mixture was stirred at rt for 5 h before water (5 mL) was added and the mixture partitioned between EtOAc (20 mL) and water (20 mL). The organic phase was washed with water (3×20 mL), brine (20 mL) and dried (MgSO₄). The solvent was removed in vacuo and the residue purified by column chromatography (0.4% NH₃: 4% MeOH: DCM) to give the title compound: RT=2.57 min; m/z (ES+)=372.2 [M+H]+.

Example 91

3-{5-[(2-Cyclohexylethylamino)methyl]pyridin-2-yl}-4-methylbenzamide

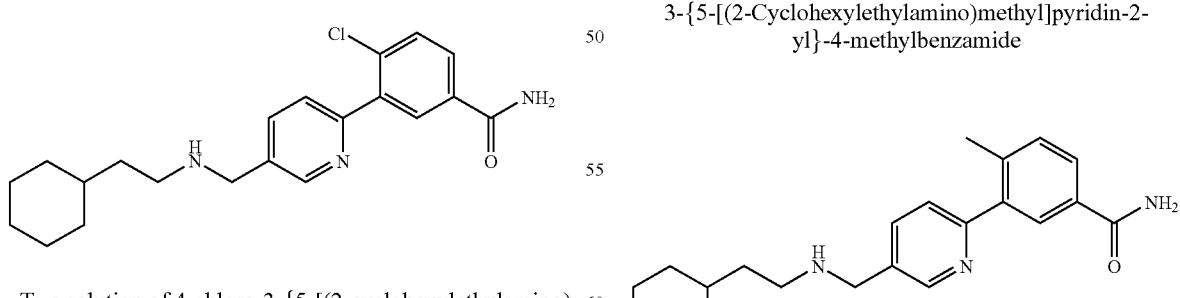

To a solution of 4-methyl-3-(4,4,5,5-tetramethyl-[1,3,2]dioxaborolan-2-yl)benzamide (Preparation 18, 150 mg, 0.57 mmol) and (6-bromopyridin-3-ylmethyl)-(2-cyclohexylethyl)amine (Preparation 15, 188 mg, 0.63 mmol) in dioxane (3 mL) was added 2M Na$_2$CO$_3$ (1 mL) and bis(diphenylphosphinoferrocene)-palladium dichloride (47 mg, 0.06 mmol). The mixture was purged with argon for 10 min and the mixture heated to 70° C. for 6 h. On cooling to rt, EtOAc (50 mL) was added and the organic phase washed with water (2×30 mL), brine (30 mL) and dried (MgSO$_4$). The solvent was removed in vacuo and the residue purified by column chromatography (0.4% NH$_3$: 4% MeOH: DCM) to give the title compound: RT=2.53 min; m/z (ES$^+$)=352.2 [M+H]$^+$.

The procedure outlined in Preparation 13 was used to prepare Examples 92 and 93 from (6-bromopyridin-3-ylmethyl)-(2-cyclohexylethyl)amine (Preparation 15) and the appropriate boronic acid.

TABLE 11

| Ex | Structure | Name | RT (min) | m/z (ES$^+$) |
|---|---|---|---|---|
| 92 | 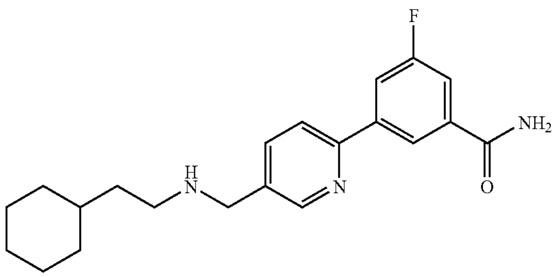 | 3-{5-[(2-Cyclohexylethylamino)methyl]-pyridin-2-yl}-5-fluoro-benzamide | 2.59 | 356.1 [M + H]$^+$ |
| 93 | 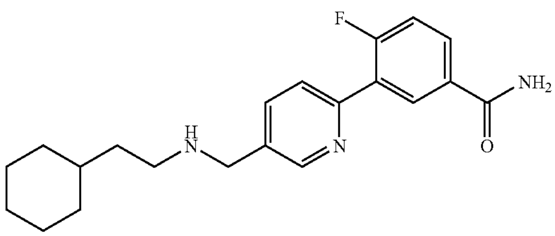 | 3-{5-[(2-Cyclohexylethylamino)methyl]-pyridin-2-yl}-4-fluoro-benzamide | 2.56 | 356.1 [M + H]$^+$ |

The biological activity of the compounds of the invention may be tested in the following assay systems:

Competition Binding Assays

Mu-, kappa- or delta-opioid receptor expressing membranes (5-15 µg/well) were suspended in 50 mM Tris buffer pH 7.6 containing 5 mM MgCl$_2$ and were incubated on 96-well plates with test compound or vehicle (1% DMSO) and either 0.5 nM $^3$H-DAMGO, 0.8 nM $^3$H-U-69,595 or 1.1 nM $^3$H-DPDPE respectively in a total volume of 200 µL for 90 min at rt (22° C.). The contents of the wells were filtered and washed 5 times with chilled 50 mM Tris buffer pH 7.6 through H$_2$O pre-soaked GF/B filters using a Perkin Elmer Filtermate. The filters were dried and upon application of scintillant the bound radioactive content for each well determined by scintillation counting in a Wallac TriLux Microbeta scintillation counter. Non-specific binding was determined in the presence of 2 µM Naloxone. IC$_{50}$ values were determined by plotting log concentration test compound against specific binding and subsequent K$_i$ values calculated.

Compounds of the invention demonstrate K$_i$ values of <10000 nM for the mu-opioid receptor in the competition binding assay and preferred compounds, such as Examples 46 and 84, have a K$_i$ of <100 nM at the mu-opioid receptor.

GTPγS Functional Binding Assays

Mu-, kappa- or delta-opioid receptor expressing membranes (5-20 µg/well) were suspended in 50 mM HEPES buffer pH 7.6 containing 3 mM MgCl$_2$, 120 mM NaCl, 150 pM GTPγS, 10 µg/mL saponin and 3 µM GDP (µ-opioid receptor assay) or 5 µM GDP (κ- and δ-opioid receptor assay) and were pre-incubated on 96-well plates with test compound or vehicle (1% DMSO) in a total volume of 160 µL for 10 min at rt (22° C.). Specific agonists DAMGO (10 nM final concentration), U-50,488 (30 nM final concentration) or SNC-80 (10 nM final concentration) were added respectively and the plates pre-incubated for a further 15 min at rt (22° C.) $^{35}$S-GTPγS at a final concentration in the assay of 150 pM was then added to provide a total volume per well of 200 µL and the plates incubated for 45 min at 30° C. The contents of the wells were filtered and washed 5 times with chilled 50 mM Tris buffer pH 7.6 through H$_2$O pre-soaked GF/B filters using a Perkin Elmer Filtermate. The filters were dried and upon application of scintillant the bound radioactive content for each well determined by scintillation counting in a Wallac TriLux Microbeta scintillation counter. Non-specific binding was determined in the presence of 10 µM GTPγS. IC$_{50}$ values were determined by plotting log concentration test compound against percentage increase over non-stimulated $^{35}$S-GTPγS binding.

Compounds of the invention demonstrate IC$_{50}$ values of <10000 nM for the mu-opioid receptor in the GTPγS assay and preferred compounds, such as Example 46 and 84, have an IC$_{50}$ of <100 nM at the mu-opioid receptor.

The compounds of the invention preferably demonstrate a degree of selectivity for modulation of the mu-opioid receptor compared to the kappa- and delta-opioid receptors.

In Vivo Feeding Study

The effect of compounds of the invention on body weight and food and water intake was examined in freely-feeding male Sprague-Dawley rats maintained on reverse-phase lighting. Test compounds and reference compounds (e.g. sibutramine) were dosed by appropriate routes of administration (e.g. intraperitoneally or orally) and measurements made over the following 24 h. Rats were individually housed in polypropylene cages with metal grid floors at a temperature of 21±4° C. and 55±20% humidity. Polypropylene trays with cage pads were placed beneath each cage to detect any food spillage Animals were maintained on a reverse phase light-dark cycle (lights off for 8 h from 09.30-17.30 h) during which time the room was illuminated by red light. Animals had free access to a standard powdered rat diet and tap water during a two week acclimatization period. The diet was contained in glass feeding jars with aluminum lids. Each lid had a 3-4 cm hole in it to allow access to the food. Animals, feeding jars and water bottles were weighed (to the nearest 0.1 g) at the onset of the dark period. The feeding jars and water bottles were subsequently measured 1, 2, 4, 6 and 24 h after animals are dosed with a compound of the invention and any significant differences between the treatment groups at baseline compared to vehicle-treated controls. Compounds of the invention demonstrated inhibition of feeding over 24 h at a dose of ≦100 mg/kg (po).

What is claimed is:

1. A compound of formula (I), or a pharmaceutically acceptable salt thereof:

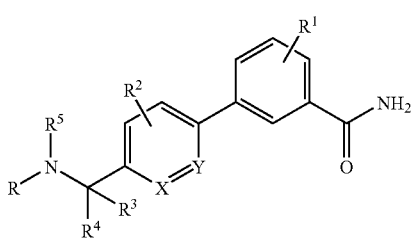

wherein X and Y are CH, or one of X and Y is N and the other is CH;
R is $(CR^7R^8)_nR^6$;
n is 0, 1, 2 or 3;
when n is 0, $R^6$ is selected from cyclopropyl, cyclobutyl, cyclopentyl, decahydronaphthyl, 1,2,3,4-tetrahydronaphthyl, and spirofused ring systems;
when n is 1, $R^6$ is selected from methyl, ethyl, propyl, isopropyl, butyl, sec-butyl, pentyl, hexyl, naphthyl, $C_5$-$C_{10}$ heteroaryl, a 4- to 7-membered oxygen containing heterocycle, cyclopropyl, cyclobutyl, cyclopentyl, decahydronaphthyl, adamantyl, indanyl, 1,2,3,4-tetrahydronaphthyl, bi-cyclic or tri-cyclic saturated carbocycle, fused or bridged ring system, cyclohexyl substituted with one to three substituents selected from $C_1$-$C_6$ alkoxy, $C_1$-$C_6$ haloalkyl, $C_1$-$C_6$ haloalkoxy and halogen, and phenyl substituted with one to three substituents selected from $C_1$-$C_6$ alkyl and $C_1$-$C_6$ alkoxy;
when n is 2, $R^6$ is selected from methyl, ethyl, propyl, butyl, sec-butyl, tert-butyl, pentyl, hexyl, cyclopropyl, cyclobutyl, cyclopentyl, decahydronaphthyl, adamantyl, indanyl, 1,2,3,4-tetrahydronaphthyl, naphthyl, bi-cyclic or tri-cyclic saturated carbocycle, fused or bridged ring system, $C_5$-$C_{10}$ heteroaryl, a 4- to 7-membered oxygen containing heterocycle, phenyl and cyclohexyl, wherein said phenyl or cyclohexyl is substituted with one to three substituents selected from $C_1$-$C_6$ alkyl, $C_1$-$C_6$ alkoxy, $C_1$-$C_6$ haloalkyl, $C_1$-$C_6$ haloalkoxy and halogen;
when n is 3, $R^6$ is selected from ethyl, propyl, isopropyl, butyl, sec-butyl, tert-butyl, pentyl, hexyl, $C_6$-$C_{10}$ aryl, $C_5$-$C_{10}$ heteroaryl, $C_3$-$C_{10}$ cycloalkyl, and a 4- to 7-membered oxygen containing heterocycle;
wherein any $R^6$ groups are optionally substituted with one to three substituents selected from $C_1$-$C_6$ alkyl, $C_1$-$C_6$ alkoxy, $C_1$-$C_6$ haloalkyl, $C_1$-$C_6$ haloalkoxy and halogen;
$R^1$ is hydrogen, $C_1$-$C_3$ alkyl or halogen;
$R^2$ is hydrogen, $C_1$-$C_3$ alkyl or halogen;
$R^3$ and $R^4$ are independently selected from hydrogen and $C_1$-$C_3$ alkyl;
$R^5$ is hydrogen, $C_1$-$C_6$ alkyl or —$C_2$-$C_3$ alkyl-O—$C_1$-$C_3$ alkyl; and $R^7$ and $R^8$ are independently selected from hydrogen and $C_1$-$C_3$ alkyl, or when n is 2 or 3 one of $R^7$ and $R^8$ may be hydroxy, provided the hydroxy group is not attached to the carbon adjacent to N—$R^5$.

2. A compound according to claim 1, or a pharmaceutically acceptable salt thereof, wherein X and Y are CH.

3. A compound according to claim 2, or a pharmaceutically acceptable salt thereof, wherein $R^2$ is hydrogen, methyl or fluoro.

4. A compound according to claim 1, or a pharmaceutically acceptable salt thereof, wherein X is N.

5. A compound according to claim 1, or a pharmaceutically acceptable salt thereof, wherein Y is N.

6. A compound according to claim 5, or a pharmaceutically acceptable salt thereof, wherein $R^2$ is hydrogen or methyl.

7. A compound according to claim 1, or a pharmaceutically acceptable salt thereof, wherein when $R^1$ is other than hydrogen it is not ortho to the amide group and para to the ring junction.

8. A compound according to claim 1, or a pharmaceutically acceptable salt thereof, wherein n is 0 and $R^6$ is optionally substituted cyclopropyl, cyclobutyl, cyclopentyl or decahydronaphthyl.

9. A compound according to claim 1, or a pharmaceutically acceptable salt thereof, wherein n is 1, 2 or 3 and $R^7$ and $R^8$ are hydrogen.

10. A compound according to claim 1, or a pharmaceutically acceptable salt thereof, wherein n is 1 and $R^6$ is optionally substituted naphthyl, $C_5$-$C_{10}$ heteroaryl, cyclopropyl, cyclobutyl, cyclopentyl, decahydronaphthyl, adamantyl, indanyl, 1,2,3,4-tetrahydronaphthyl, bi-cyclic or tri-cyclic saturated carbocycle, fused or bridged ring system, cyclohexyl substituted with one to three substituents selected from $C_1$-$C_6$ alkoxy, $C_1$-$C_6$ haloalkyl, $C_1$-$C_6$ haloalkoxy and halogen, or phenyl substituted with one to three substituents selected from $C_1$-$C_6$ alkyl and $C_1$-$C_6$ alkoxy.

11. A compound according to claim 1, or a pharmaceutically acceptable salt thereof, wherein n is 2 and $R^6$ is optionally substituted cyclopropyl, cyclobutyl, cyclopentyl, decahydronaphthyl, adamantyl, indanyl, 1,2,3,4-tetrahydronaphthyl, naphthyl, bi-cyclic or tri-cyclic saturated carbocycle, fused or bridged ring system, $C_5$-$C_{10}$ heteroaryl, or a 4- to 7-membered oxygen containing heterocycle.

12. A compound according to claim 1, or a pharmaceutically acceptable salt thereof, wherein n is 3 and $R^6$ is optionally substituted $C_6$-$C_{10}$ aryl or $C_3$-$C_{10}$ cycloalkyl.

13. A compound according to claim 1, or a pharmaceutically acceptable salt thereof, wherein $R^3$ and $R^4$ are hydrogen.

14. A compound according to claim 1, or a pharmaceutically acceptable salt thereof, wherein $R^5$ is hydrogen or methyl.

15. A compound selected from the group consisting of:
4'-[(4-Methylcyclohexylamino)methyl]biphenyl-3-carboxylic acid amide;
4'-Cyclohexylamino-methylbiphenyl-3-carboxylic acid amide;
4'-[(2-Cyclopentyl-ethylamino)methyl]-biphenyl-3-carboxylic acid amide;
4'-[(3-Phenyl-propylamino)methyl]-biphenyl-3-carboxylic acid amide;
4'-[(3-Methyl-benzylamino)methyl]-biphenyl-3-carboxylic acid amide;
4'-[(4-Trifluoro-methoxybenzylamino)-methyl]biphenyl-3-carboxylic acid amide;

4'-[(3,4-Dichloro-benzylamino)methyl]-biphenyl-3-carboxylic acid amide;
4'-[(4-Chlorobenzyl-amino)methyl]-biphenyl-3-carboxylic acid amide;
4'-{[(Methyl-(3-methyl-butyl)amino]methyl}-biphenyl-3-carboxylic acid amide;
4'-[(3-Cyclohexyl-propylamino)methyl]-biphenyl-3-carboxylic acid amide;
4'-Pentylaminomethyl-biphenyl-3-carboxylic acid amide;
4'-{[(Benzo[b]-thiophen-3-ylmethyl)-amino]methyl}-biphenyl-3-carboxylic acid amide;
4'-[(2-Thiophen-2-yl-ethylamino)methyl]-biphenyl-3-carboxylic acid amide;
4'-Hexylaminomethyl-biphenyl-3-carboxylic acid amide;
4'-[(3,3-Dimethyl-butylamino)methyl]-biphenyl-3-carboxylic acid amide;
4'-{[2-(4-Chloro-phenyl)ethylamino]-methyl}biphenyl-3-carboxylic acid amide;
4'-{[2-(4-Fluoro-phenyl)ethylamino]-methyl}biphenyl-3-carboxylic acid amide;
4'-{[2-(3,4-Dichloro-phenyl)ethylamino]-methyl}biphenyl-3-carboxylic acid amide;
4'-{[(Naphthalen-1-ylmethyl)amino]-methyl}biphenyl-3-carboxylic acid amide;
4'-{[2-(3-Fluoro-phenyl)ethylamino]-methyl}biphenyl-3-carboxylic acid amide;
4'-{[2-(3-Trifluoro-methylphenyl)ethyl-amino]methyl}-biphenyl-3-carboxylic acid amide;
4'-[(2-Thiophen-3-yl-ethylamino)methyl]-biphenyl-3-carboxylic acid amide;
4'-{[2-(4,4-Difluorocyclohexyl)ethylamino]methyl}biphenyl-3-carboxylic acid amide;
4'-[(2-Cyclohexyl-ethylamino)methyl]-3'-fluorobiphenyl-3-carboxylic acid amide;
3'-Fluoro-4'-(phenethyl-aminomethyl)-biphenyl-3-carboxylic acid amide;
3'-Chloro-4'-[(2-cyclohexylethyl-amino)methyl]-biphenyl-3-carboxylic acid amide;
3'-Chloro-4'-(phenethylamino-methyl)biphenyl-3-carboxylic acid amide;
3-{6-[(3-Methyl-butylamino)methyl]-pyridin-3-yl}benzamide;
3-[6-(Benzylamino-methyl)pyridin-3-yl]-benzamide;
3-[6-(Phenethylamino-methyl)pyridin-3-yl]-benzamide;
3-{6-[(2-Cyclohexyl-ethylamino)methyl]-pyridin-3-yl}benzamide;
4'-[(2-Cyclohexyl-ethylamino)methyl]-2'-fluorobiphenyl-3-carboxylic acid amide;
2'-Fluoro-4'-(phenethyl-aminomethyl)biphenyl-3-carboxylic acid amide;
4'-[(2-Adamantan-2-yl-ethylamino)methyl]-2'-methylbiphenyl-3-carboxylic acid amide;
4'-[(4-tert-Butyl-cyclohexylamino)-methyl]-2'-methyl-biphenyl-3-carboxylic acid amide;
4'-[(2-Bicyclo[2.2.1]-hept-2-yl-ethylamino)-methyl]-2'-methyl-biphenyl-3-carboxylic acid amide;
4'-[(4-Isopropyl-cyclohexylamino)-methyl]-2'-methyl-biphenyl-3-carboxylic acid amide;
4'-[(2-Cyclohexyl-ethylamino)methyl]-2'-methylbiphenyl-3-carboxylic acid amide;
2'-Methyl-4'-(phenethylamino-methyl)biphenyl-3-carboxylic acid amide;
4'-[(2-Cyclohexyl-ethylamino)methyl]-3'-methylbiphenyl-3-carboxylic acid amide;
3'-Methyl-4'-(phenethylamino-methyl)biphenyl-3-carboxylic acid amide;
cis-4'-[(4-tert-Butylcyclohexylamino)methyl]-2'-fluoro-biphenyl-3-carboxylic acid amide;
trans-4'-[(4-tert-Butylcyclohexylamino)methyl]-2'-fluorobiphenyl-3-carboxylic acid amide;
4'-[(Methylphenethyl-amino)methyl]-biphenyl-3-carboxylic acid amide;
4'-{[2-Cyclohexyl-ethyl)methylamino]-methyl}biphenyl-3-carboxylic acid amide;
3-[5-(Phenethylaminomethyl)pyridin-2-yl]benzamide;
3-{5-[(3-Methyl-butylamino)methyl]-pyridin-2-yl}benzamide;
3-{5-[(2-Cyclohexyl-ethylamino)methyl]-pyridin-2-yl}benzamide;
3-[5-(Benzylamino-methyl)pyridin-2-yl]-benzamide;
3-{5-[(3,4-Dichloro-benzylamino)methyl]-pyridin-2-yl}benzamide;
3-(5-{[(Benzo[b]-thiophen-3-ylmethyl)-amino]methyl}pyridin-2-yl)benzamide;
3-{5-[(3-Methylcyclo-hexylamino)methyl]-pyridin-2-yl}benzamide;
trans-3-{5-[(4-Isopropylcyclohexyl-amino)methyl]-pyridin-2-yl}benzamide;
cis-3-{5-[(4-Isopropyl-cyclohexylamino)-methyl]pyridin-2-yl}-benzamide;
3-{5-[(4-Ethylcyclo-hexylamino)methyl]-pyridin-2-yl}benzamide;
trans-3-{5-[4(4-tert-Butylcyclohexyl-amino)methyl]pyridin-2-yl}benzamide;
3-{5-[(4,4-Dimethyl-cyclohexylamino)-methyl]pyridin-2-yl}-benzamide;
3-{5-[(4-Methylcyclo-hexylamino)methyl]-pyridin-2-yl}benzamide;
4-Fluoro-3-[5-(phenethylaminomethyl)pyridin-2-yl]benzamide;
3-[3-Methyl-5-(phenethylamino-methyl)pyridin-2-yl]-benzamide;
3-{5-[(2-Cyclohexyl-ethylamino)methyl]-3-methylpyridin-2-yl}-benzamide;
3-{5-[(4,4-Dimethyl-cyclohexylamino)-methyl]-3-methyl-pyridin-2-yl}benzamide;
Trans-3-{5-[(4-tert-Butylcyclohexyl-amino)methyl]-3-methylpyridin-2-yl}-benzamide;
3-{5-[(4-Isopropyl-cyclohexylamino)-methyl]-3-methyl-pyridin-2-yl}benzamide;
3-(5-{[2-(2-Chloro-phenyl)ethylamino]-methyl}-3-methyl-pyridin-2-yl)benzamide;
3-{5-[(2-Bicyclo[2.2.1]hept-2-ylethylamino)methyl]pyridin-2-yl}benzamide;
3-(5-{[Adamantan-1-ylmethylamino]-methyl}pyridin-2-yl)-benzamide;
3-{5-[(2-Adamantan-1-ylethylamino)methyl]-pyridin-2-yl}benzamide;
3-(5-{[2-(4-Methyl-cyclohexyl)ethyl-amino]methyl}pyridin-2-yl)benzamide;
3-{5-[(2-Adamantan-2-ylethylamino)methyl]-pyridin-2-yl}benzamide;
3-{5-[(2-Cycloheptyl-ethylamino)methyl]-pyridin-2-yl}benzamide;
3-(5-{[2-(3-Methyl-cyclohexyl)ethyl-amino]methyl}pyridin-2-yl)benzamide;
3-[5-(Adamantan-1-ylaminomethyl)-pyridin-2-yl]benzamide;
Cis-3-{5-[(4-tert-Butyl-cyclohexylamino)-methyl]pyridin-2-yl}-benzamide;
3-{5-[(2-Adamantan-2-ylethylamino)methyl]-3-methylpyridin-2-yl}-benzamide;

4-Chloro-3-{5-[(2-cyclohexylethylamino)methyl]pyridin-2-yl}benzamide;

3-{5-[(2-Cyclohexylethylamino)methyl]pyridin-2-yl}-4-methylbenzamide;

3-{5-[(2-Cyclohexyl-ethylamino)methyl]-pyridin-2-yl}-5-fluoro-benzamide;

3-{5-[(2-Cyclohexyl-ethylamino)methyl]-pyridin-2-yl}-4-fluoro-benzamide;

and pharmaceutically acceptable salts thereof.

16. A pharmaceutical composition comprising a compound according to claim 1, or a pharmaceutically acceptable salt thereof, and a pharmaceutically acceptable carrier.

17. A method for the treatment of obesity comprising a step of administering to a subject in need thereof an effective amount of a compound according to claim 1, or a pharmaceutically acceptable salt thereof.

18. A method for the regulation of food intake and/or satiety or for the treatment of obesity comprising a step of administering to a subject in need thereof an effective amount of a compound according to claim 1, or a pharmaceutically acceptable salt thereof.

19. A method for the treatment of metabolic diseases selected from the group consisting of Type II diabetes, metabolic syndrome (syndrome X), impaired glucose tolerance, dyslipidemia, hyperlipidemia, hypertriglyceridemia, hypercholesterolemia, low HDL levels or hypertension, comprising a step of administering to a subject in need thereof an effective amount of a compound according to claim 1, or a pharmaceutically acceptable salt thereof.

20. A method for the treatment of substance abuse, alcohol abuse, compulsive gambling, depression, opiate overdose, septic shock, irritable bowel syndrome, nausea, vomiting and stroke, comprising a step of administering to a subject in need thereof an effective amount of a compound according to claim 1, or a pharmaceutically acceptable salt thereof.

21. A compound according to claim 4, or a pharmaceutically acceptable salt thereof, wherein $R^2$ is hydrogen or methyl.

* * * * *